US006051576A

United States Patent [19]
Ashton et al.

[11] Patent Number: 6,051,576
[45] Date of Patent: Apr. 18, 2000

[54] MEANS TO ACHIEVE SUSTAINED RELEASE OF SYNERGISTIC DRUGS BY CONJUGATION

[75] Inventors: Paul Ashton, Boston, Mass.; Peter Anthony Crooks, Lexington, Ky.; Tadeusz Cynkowski, Lexington, Ky.; Grazyna Cynkowska, Lexington, Ky.; Hone Guo, Malden, Mass.

[73] Assignee: University Of Kentucky Research Foundation, Lexington, Ky.

[21] Appl. No.: 08/791,071

[22] Filed: Jan. 29, 1997

Related U.S. Application Data

[63] Continuation of application No. 08/388,855, Feb. 15, 1995, abandoned, which is a continuation-in-part of application No. 08/187,462, Jan. 28, 1994.

[51] Int. Cl.$^7$ .................................................. A61K 31/495
[52] U.S. Cl. ............................................ 514/255; 514/597
[58] Field of Search ...................................... 514/255, 597

[56] References Cited

U.S. PATENT DOCUMENTS

| | | | |
|---|---|---|---|
| 4,194,581 | 3/1980 | Leong | 528/398 |
| 4,267,326 | 5/1981 | Ozaki et al. | 544/313 |
| 4,489,065 | 12/1984 | Walton et al. | 424/180 |
| 4,897,260 | 1/1990 | Ross et al. | 424/59 |
| 4,910,192 | 3/1990 | Avery et al. | 514/180 |
| 4,933,324 | 6/1990 | Shashoua | 514/17 |
| 4,975,278 | 12/1990 | Senter et al. | 424/94.3 |
| 5,057,301 | 10/1991 | Wilbur et al. | 424/1.1 |
| 5,104,877 | 4/1992 | Boger | 514/256 |
| 5,112,835 | 5/1992 | Miyasaka et al. | 544/302 |
| 5,130,126 | 7/1992 | Koyama et al. | 424/78.18 |
| 5,171,566 | 12/1992 | Mizushima et al. | 424/78.04 |
| 5,176,907 | 1/1993 | Leong | 424/78.08 |
| 5,177,064 | 1/1993 | Bodor | 514/51 |

OTHER PUBLICATIONS

Chemical Abstracts AN 1989: 454065, Jones et al, 1989.

Kellen et al., Anticancer Research, vol. 8, p. 1373–76 (1988).

Gagliardi et al., Cancer Research, vol. 52, p. 5073–75 (Sep. 15, 1992).

Chemical Abstracts, vol. 117 (8), Abstract No. 76315m. 1992.

Chemical Abstracts, vol. 116 (18), Abstract No. 181046b. 1992.

Collins et al., "Inhibition of Angiogenesis by Suramin", Cancer Research, vol. 52, pp. 5073–5075, Sep. 15, 1992.

Suramin Merck Index, 11th Ed., Merck and Col, Inc., 1989, Abstracts 417 and 8696.

Jones, R. N., "In Vitro Activity of Ro 24–6392, a Novel Ester–Linked Co–Drug Combining Ciprofloxacin and Desacetylcefotaxime", Eur. J. Clin. Microbiol. Infect Dis., vol. 9, 1990, pp. 435–438.

Segawa et al., "Effect of a New Non–steroidal Anti–inflammatory Combination of a Histamine $H_2$ Antagonist and Indometacin on Gastroduodenal Muscosal Membrane in Rat", Arzneimittel–Forschung Drug Research, 1992, vol. 42, No. 10, pp. 1171–1270.

Jones, Ronald N., "Impact of Changing Pathogens and Antimicrobial Susceptibility Patterns in the Treatment of Serious Infections in Hospitalized Patients", Symposium on Antimicrobial Therapy, The American Journal of Medicine, Jun. 24, 1996, vol. 100, pp. (6A–3S)–(6A–12S).

Jones, R. N., "Isepamicin (SCH 21420, 1–N–HAPA Gentamicin B): Microbiological Characteristics Including Antimicrobial Potency and Spectrum of Activity", Journal of Chemotherapy, vol. 7, pp. 7–16.

Dose et al., "Physiological and Behavioral Effects of Early Embryonic Exposure to Ethanol and Cocaine in the Young Chick", Neurotoxicology and Teratology, 1995, vol. 17, No. 1, pp. 49–55.

Casteels–Josson et al., "Acute Transcriptional Response of the Honeybee Peptide–Antibiotics Gene Repertoire and Required Post–transnational Conversion of the Precursor Structures", The Journal of Biological Chemistry, Nov. 18, 1994, vol. 269, No. 46, pp. 28569–28575.

Knisely et al., "Effects of Carbon Monoxide in Combination With Behaviorally Active Drugs on Fixed–Ration Performance in the Mouse", Neurotoxicology and Teratology, 1989, vol. 11, pp. 447–452.

Jones et al., "In Vitro Activity of Clarithromycin (TE–031, A–67268) and 14OH–Clarithromycin Alone and in Combination against Legionella Species", Eur. J. Clin. Microbiol. Infect. Dis., vol. 9, pp. 846–848.

Jones et al., "In Vitro Activity of Ro 23–9424, Ceftazidime, and Eight Other Newer Beta–Lactams Against 100 Gram–Positive Blood Culture Isolates", Diagnostic Microbiology and Infectious Disease, vol. 12, No. 2, Mar./Apr. 1989, pp. 143–147.

Fuchs et al., "Evaluation of Disk Susceptibility Testing of Cefotaxime/Desacetylcefotaxime", Diagnostic Microbiology and Infectious Disease, vol. 12, No. 1, Jan./Feb. 1989, pp. 81–85.

Jones et al., "Piperacillin/Tazobactam (YTR 830) Combination", Diagnostic Microbiology and Infectious Disease, vol. 12, No. 6, Nov./Dec. 1989, pp. 489–494.

Jones, Ronald N., "Cefotaxime and Desacetylcefotaxime Antimicrobial Interactions", Diagnostic Microbiology and Infectious Disease, vol. 22, No. 1–2, May/Jun. 1995, pp. 19–33.

Jones, Ronald N., "Broth–Disk Elution Tests to Predict the Susceptibility of Anaerobic Bacteria to the Ampicillin–Sulbactam Combination", Diagnostic Microbiology and Infectious Disease, vol. 13, No. 4, Jul./Aug. 1990, 353–355.

*Primary Examiner*—Keith D. MacMillan
*Attorney, Agent, or Firm*—McDermott, Will & Emery

[57] ABSTRACT

A codrug composition of at least two drug compounds covalently linked to one another via a labile bond to form a single codrug composition, or ionically linked to one another to form a single workings composition, and methods of use of the codrug for the treatment of various medical conditions. The codrug may be administered by itself or in the form of a bioerodible or nonbioerodible substance.

37 Claims, 3 Drawing Sheets

MEANS TO ACHIEVE SUSTAINED RELEASE OF SYNERGISTIC DRUGS BY CONJUGATION

This application is a continuation of U.S. Ser. No. 08/388,855, filed Feb. 15, 1995, abandoned, which is a continuation-in-part of U.S. Ser. No. 08/187,462, filed Jan. 28, 1994.

TECHNICAL FIELD

The present invention is related to the field of controlled pharmaceutical delivery, Especially to codrug compounds.

BACKGROUND ART

A prodrug is a compound formed by chemical modification of a biologically active compound which will liberate the active compound in vivo by enzymatic or hydrolytic cleavage. The primary purpose of employing a prodrug for oral administration is to increase intestinal absorption or site specific absorption or to reduce local side effects, such as gastrointestinal irritation. Prodrugs may also be used to increase transdermal absorption, by enhancing permeation through topical membranes.

On this basis, prodrugs are not generally classified as sustained release dosage forms. However, the ability to bioreversibly modify the physicochemical properties of a drug allows better intestinal transport properties and hence can influence the drug blood levels versus time profile of the pharmaceutical compound. Thus, prodrugs can be used to increase the strategies for sustained release and, in a limited sense, can be sustaining in their own right.

U.S. Pat. No. 5,176,907 to Leong et al. discloses biocompatible and biodegradable poly(phosphoester-urethanes). The patent describes therapeutic agent delivery vehicles which include polymers which are biodegradable because of the hydrolyzable phosphoester or P—(O)—O—C bond. A particular aspect of the Leong patent is a therapeutic agent that can be .Introduced into the poly-phosphoester urethane by covalently binding a radical of this therapeutic agent to the phosphorous atom of the polymer. The patent describes attaching 5-fluorouracil to polyurethane. The patent discloses that drugs with carboxyl groups can be coupled to the phosphorous atom via an ester bond which is hydrolyzable.

U.S. Pat. No. 5,194,581 to Leong et al. discloses biodegradable polyphosphoesters. A therapeutic agent is pendently bound to a poly(phosphoester) polymeric matrix. When the therapeutic agent is pendently attached, it is chemically linked through, for example, ionic or covalent bonding. The drug is released when the polymeric agent biodegrades. A combination of one or more therapeutic agents can be incorporated into the composition of the invention. The patent discloses therapeutic agents containing two hydroxyl groups that can be directly incorporated into the backbone of the polymers. Other therapeutic agents can be derivatized for incorporation into the backbone. For instance, a drug with two amino groups can be reacted with the carboxyl group of a hydroxyl carboxylic acid. The hydroxyl groups can then be used to form the poly (phosphoester). A sustained delivery is effected by the hydrolysis of the polymeric prodrug. Although Leong discloses that two therapeutic agents may be bound to a polymer matrix via covalent bonding, he does not disclose or suggest that two therapeutic agents can be linked to one another by covalent bonding as a prodrug as in the present invention.

U.S. Pat. No. 5,104,877 to Boger discloses a psoriasis treatment. Boger describes a carboxy-protecting group used as a prodrug where the carboxy-protecting group can be readily cleaved in vivo. These carboxy protecting groups are indicated to be used in the protection of carboxyl groups in penicillin and cephalosporin.

U.S. Pat. No. 4,489,065 to Walton et al., discloses chondroitin drug complexes. The '065 patent describes that the rate of drug release can be controlled in a variety of ways, such as by encapsulation in a material which dissolves slowly in the body fluids, by entrapment in a bolus or matrix from which the drug diffuses slowly, or by conversion into a so called "prodrug", in which the drug is bound with another substance turning it into a substantially inactive compound or complex. The drug is gradually released by physiological action when injected into the tissues of the patient. The '065 patent discloses chondroitin or chondroitin sulphate covalently or ionically bonded to a drug substance of the group consisting of chloramphenicol, methotrexate, adriamycin, vinblastine, vincristine, vindesine, 6-mercaptopurine, 5-fluorouracil, penicillin antibiotics, cephalosporin antibiotics, and oxacephalosporin antibiotics, to form a prodrug. The patent states that the prodrug provides controlled release of the drug in a physiological environment. The patent discloses that a variety of functional groups are available in chondroitan for covalently bonding (particularly carboxyl, COOH, and hydroxyl, OH) and for ionic bonding (sulfate —$OSO_3$—, and carboxylate, —COO—) with drugs. Covalent bonding can be by way of ester links, —COOY, or amide links, —CONHY—. When chondroitin and the drug substance contain a hydroxyl and an amino group, the reaction can proceed through the formation of a carbamate bond via activation of the hydroxyl to a chloroformate moiety with subsequent linking to the amine function. The rate of release of the drug from the chondroitin or from the linking substance is dependent on the type of bonds chosen for linkage.

U.S. Pat. No. 5,130,126 to Koyama et al. discloses a polymer-drug conjugate and a method of producing it. Polymers which may be used have an alkyleneoxy group as a repeating unit such as polyoxyalkylene glycol as well as polymers obtained by substituting the terminal groups of the polymers with an acyl, amino or allyl group. Polymers are combined with drugs using covalent bonding, ionic bonding, coordinate bonding, and shiff base formation.

U.S. Pat. No. 5,057,301 to Wilbur et al. discloses modified cellular substrates used as linkers for increased cell retention of diagnostic and therapeutic agents. The invention of Wilbur et al. comprises a ligand-linker conjugate wherein the linker is a chemically modified cellular substrate having a protein conjugation group attached thereto. The protein conjugation group attached to the modified substrate linker is a functional group which will react with the group on the targeting protein and form a bond between the linker and the protein. Suitable protein conjugation groups include active esters (including carboxylic esters, imide esters, succinimidyl esters, phenolic esters, and imidate esters), primary or secondary amines, hydrazides, hydrazines, carboxylate, isothiocyanates, isocyanates, and Michael-type acceptor groups such as maleimides, thiols, anhydrides and alkyl halides.

U.S. Pat. No. 5,171,566 to Mizushima et al. discloses a flurbiprofen derivative ophthalmic preparation. The derivative is an ester of flurbiprofen. U.S. Pat. No. 4,933,324 to Shashoua is directed to a fatty acid-neuroactive drug conjugate used as a prodrug and involves the formation of a prodrug from a fatty acid carrier and a neuroactive drug. The bond between the fatty acid and the drug may be an amide or an ester bond. U.S. Pat. No. 4,975,278 to Senter et al.

discloses antibody-enzyme conjugates in combination with prodrugs for the delivery of cytotoxic agents to tumor cells.

U.S. Pat. No. 4,267,326 to Ozaki et al. discloses uracil derivatives. The uracil derivatives are prepared by reacting 5-fluorouracil with an α-haloalkyl carboxylate or an aldehyde diacylate.

U.S. Pat. No. 4,897,260 to Ross et al. discloses glucocorticoid carboxylic acid esters which include triamcinolone acetonide 21-oic methylester for the treatment of xeroderma pigmentosum.

U.S. Pat. No. 4,910,192 to Avery et al. discloses topically active steroidal anti-inflammatory agents. The agents are 12-β substituted glucocorticoids wherein the 12 substituent is a hydroxyl group or a lipophilic group attached to a 12-β-hydroxyl group. The lipophilic group may be selected from an alkyl or aryl substituted ester, an ester, a carbamate and a carbonate groups. The 12th substituent can be a lower carboxylic acid ester of a 12-β-hydroxy group.

U.S. Pat. No. 5,177,064 to Bodor discloses targeted drug delivery via phosphonate derivatives. U.S. Pat. No. 5,112,835 to Miyasaka et al. discloses 6-substituted acyclopyrimidine nucleoside derivatives for use as antiviral agents. Chemical Abstracts, Volume 117(8), abstract no. 76315(m) discloses the stereoselective enzymatic hydrolysis of various ester prodrugs of ibuprofen and flurbiprofen.

Chemical Abstracts, Volume 116(18), abstract no. 181046 (b) describes the preparation of prodrugs of flurbiprofen, its 1,2-ethanediol ester and 1,4-butanediol ester. The prodrugs showed high stability in simulated gastric fluid, simulated intestinal fluid and simulated pancreatic fluid. The drugs showed less toxicity and increased anti-inflammatory and analgesic effects.

None of the above patents disclose or suggest prodrug conjugates of two or more of the same or different drugs linked to one another. Nor do they disclose codrug conjugates which are linked by reversible covalent bonds, such as ester, carbamate and carbonate bonds, so that at the desired site in the body they are cleaved to regenerate the active forms of each of the drugs.

Patient compliance in consumption of pharmaceutical compositions as part of a therapeutic regimen is critical for patient recovery and treatment. This is especially critical in elderly patients who may have poor memory and who exhibit poor patient compliance with a therapeutic regimen of doses of pharmaceutical compositions. Other high risk compliance groups include drug addicts, alcoholics and those requiring long term therapy, for example tuberculosis patients.

Furthermore, known erodible, implantable pharmaceutical substances such as polylactic acid and polyurethane compounds are formulated such that it is difficult to achieve high drug loading and hence difficult to deliver large doses of drug from the substrate. Such drug substances have low solubility.

There is a need in the pharmaceutical arts for pharmaceutical compounds which deliver two or more drugs at a single time in a single dose, which exhibit controlled drug delivery. In one embodiment, the pharmaceutical compounds of the present invention are delivered in a totally erodible drug delivery device capable of delivering two or more synergistic drugs over a prolonged period. The codrug compounds of the present invention have the advantage that linking the two drug compounds decreases the solubility of each through the carbamate, carbonate and ester bonds linking the compounds. The codrug compounds of the invention have a high degree of chemical or enzymatic lability at physiological pH 7.4.

DISCLOSURE OF THE INVENTION

Figure 1:
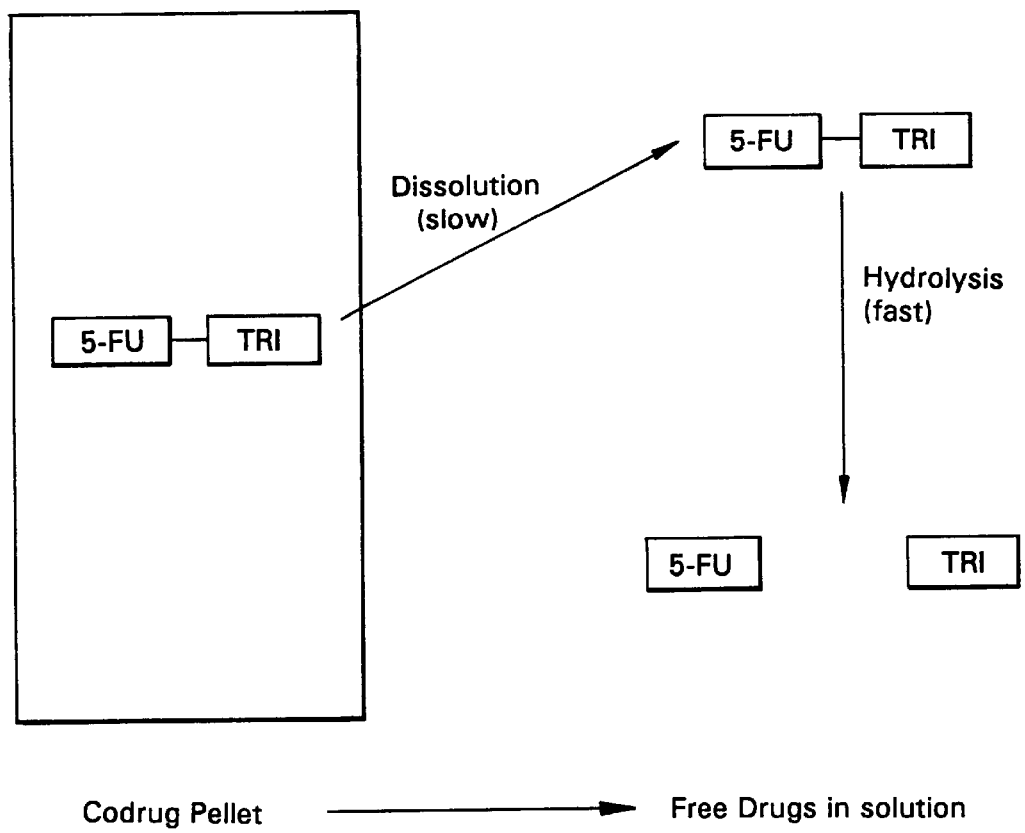
FIG. 1 shows a typical release mechanism. Amongst the advantages of these systems are that as no polymers are required to control release so the devices can be extremely small (small enough to be fitted onto a haptic of an intraocular lens) (IOLs).

An object of the invention provides sustained release delivery of two or more pharmacologically active compounds. The drug compounds may be the same or different.

Also provided for is a codrug composition, comprising at least two drug compounds covalently linked to one another via a labile bond to form a single codrug composition.

Also provided for is a codrug composition wherein drug compounds may be linked by labile bonds to another entity such as polyethylene glycol, glycerol or a sugar.

An object of the invention providers a codrug wherein at least one or more of the drug compounds is selected from the group consisting of an antiviral compound, a beta-blocker, an antibacterial compound, and a biological compound with pharmacological activity.

The invention provides a codrug composition in solid form, a codrug composition which is applied topically for examples in a form selected from the group consisting of a transdermal patch, ointment, cream, suspension, liquid and eyedrop.

A codrug according to the invention may be administered by a method selected from the group consisting of injection, inhalation, implantation, applied nasally such as a nasal spray, applied rectally, ingested orally and applied vaginally.

Another embodiment of the invention provides a codrug composition attached to a surgically implantable device, for example, a codrug attached to a suture. Another embodiment of the invention provides a codrug composition is in the form of a nonerodible delivery vehicle which for example comprises polyvinyl alcohol.

The codrug of the invention may comprise from 0.1 to up to about 100% of said nonerodible delivery vehicle.

Another object of the invention is to provide local delivery of two or more synergistic pharmacologic agents or delivery of two or more non-synergistic pharmacologic agents.

Another object of the invention provides an insoluble codrug of TRI linked to 5FU. Another object of the invention provides an insoluble codrug of flurbiprofen (FB) with 5FU.

Another object of the invention provides an insoluble codrug of acyclovir (ACV) with FB. Another object of the invention is to produce an insoluble codrug of an angiostatic steroid, 3α,17α-21-trihydroxy-5β pregnane-20-one (THS), with 5FU. Another object of the invention is to produce an insoluble codrug of prostaglandin F2 alpha (PGF2α) with timolol (TM). Another object of the invention provides 5FU linked to two molecules of FB, while another object provides THS linked to 5FU and FB.

The totally erodible drug delivery device is capable of delivering two or more synergistic drugs over a prolonged period.

Another object of the invention is to control the release rate of 5FU and triamcinolone from pellets of 5FU/TRI in a buffer.

Still another object of the invention is directed to the use of codrugs in the inhibition of posterior capsular opacification (PCO) after extracapsular cataract extraction and intraocular lens implantation.

A further object of the invention investigates the feasibility of codrug technology as a means to achieve the intravitreal delivery of 3α,17α-21-trihydroxy-5β pregnane-20-one (THS), a model angiogenesis inhibiting steroid, and 5FU.

Another object of the invention provides a totally bio-erodible sustained release system for 5FU and triamcinolone in the eye.

An additional object of the invention provides a codrug which is a salt of amiloride and suramin which inhibits angiogenesis and a method of use of this codrug to inhibit angiogenesis.

DESCRIPTION OF THE INVENTION

The present invention provides a means of improving the pharmaceutical and pharmacological properties of pharmacologically active compounds or prodrugs by conjugating them together to form a codrug.

Codrugs are formed by conjugation of two or more agents via a labile linkage. Codrug conjugates may be linked via reversible covalent bonds such as ester, carbonate, cyclic phosphate ester and carbamate bonds, so that at the required site in the body they are cleaved to regenerate the active forms of the drug compounds. Bonds may be, but are not limited to the type

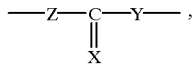

wherein Z is O, N, $CH_2$, $CH_2O$ or $CH_2S$, Y is O, or N, and X is O or S. The rate of cleavage of the two drugs can be controlled by the type of bond, the choice of drugs and the physical form of the conjugate. The bond selected may be enzyme-specific. The bond may be selected from enzymatically labile bonds, for example, to esterases as in the ACV-FB linkage, or may be chemically labile (eg. base catalyzed hydrolysis of the 5FU-TRI linkage). The codrugs are labile in water, serum or other bodily fluids and regenerate the active parent drugs. The present invention is the first to combine two or more drugs in the form of a codrug which generates two active drug compounds with improved pharmaceutical properties.

In an embodiment of the present invention, codrugs have the applicability of providing a controlled or sustained release for a systemic or local pharmacologic or physiologic effect relating to the following areas: treatment of cancerous primary tumors; chronic pain; tuberculosis; arthritis; rheumatic conditions; hormonal deficiencies such as diabetes; and modifications of the immune response such as in the prevention of transplant rejection and in cancer therapy. A wide variety of disease states may be prevented or treated using the codrug compositions of the present invention. Such disease states are known to those of ordinary skill in the art (see Goodman and Gilman, *The Pharmacological Basis of Therapeutics,* 8th Ed., Pergamon Press, NY, 1990; and *The Merck Index,* 11th Ed., Merck and Co., Inc., Rahway, N.J. 1989; incorporated herein by reference in their entireties).

In addition, codrug compositions of the present invention are suitable for treating mammalian organisms infected with the AIDS virus, manifestations of AIDS such as Kaposi's sarcoma, and AIDS related opportunistic infections such as cytomegalovirus retinitis, toxoplasmosis, Pneumocystis carnii and microbacterial avium intracellular.

A codrug of the invention may consist of one or more pharmacologically active compounds in the following classes of agents; anesthetics and pain killing agents such as lidocaine and related compounds and benzodiazepain and related compounds; anticancer agents such as 5-fluorouracil, adriamycin and related compounds; anti-inflammatory agents such as 6-mannose phosphate; anti-fungal agents such as fluconazole and related compounds; antiviral compounds such as trisodium phophomonoformate, trifluorothymidine, acyclovir, ganciclovir, dideoxyinosine (ddI), dideoxycytidine (ddC); cell transport/mobility impeding agents such as colchicine, vincristine, cytochalsian B and related compounds; anti-glaucoma drugs such as carbonic anhydrase inhibitors, beta blockers, miotics, cholinesterase inhibitors, and sympathomimetics; immunological response modifiers such as muramyl dipeptide and related compounds; cytokines and peptides/proteins such as cyclosporin, insulin, growth factor or growth hormones and steroids. Non steroidal anti-inflammatory agents include, for example, flurbiprofen and indomethacin.

Codrugs may also be formed of unstable drugs and other compounds to improve their stability such as levodopa and the peripheral decarboxylase inhibitor benserazide.

Codrug formulations may comprise a number of other substituents to optimize release, bioavailability or appearance and may be used in sustained release devices or systems. Such substituents are known to those of ordinary skill in the art and for example are set forth in *Remington's Pharmaceutical Sciences,* 18th Ed., Mack Publishing Co., Easton, Pa., 1990.

Another embodiment of the p)resent invention comprises a codrug compound in a nonerodible matrix or reservoir system containing natural or synthetic polymers that are biologically compatible with and essentially insoluble in body fluids. Such materials include for example, but are not limited to polyvinyl acetate, polyvinyl alcohol, cross-linked polyvinyl butyrate, ethylene ethyl acrylate copolymer, polyethyl hexyl acrylate, polyvinyl chloride, polyvinyl acetals, plasticized ethylene vinyl acetate copolymer, ethylene vinyl chloride copolymer, polyvinyl esters, polyvinyl butyrate, polyvinyl formal, polyamides, polymethyl-methacrylate, polybutyl methacrylate, plasticized polyvinyl chloride, plasticized nylon, plasticized soft nylon, plasticized polyethylene terethphalate, natural rubber, polyisoprene, polyisobutylene, polybutadiene, polyethylene, polytetrafluoroethylene, polyvinylidine, chloride, polyacrylonitrile, cross-linked polyvinyl pyrrolidone, polytrifluorochloroethylene, chlorinated polyethylene, poly (1,4,-isopropylidne diphenylene carbonate), vinylidine chloride, acrylonitrile copolymer, vinyl chloride-diethyl fumarate copolymer, silicone rubbers (especially medical grade polydimethylsiloxanes, ethylene-propylene rubber, silicone-carbonate copolymers, vinylidine chloride-vinyl chloride copolymer, vinyl chloride-acrylonitrile copolymer and vinylidine chloride acrylonitrile copolymer.

Figure 5:
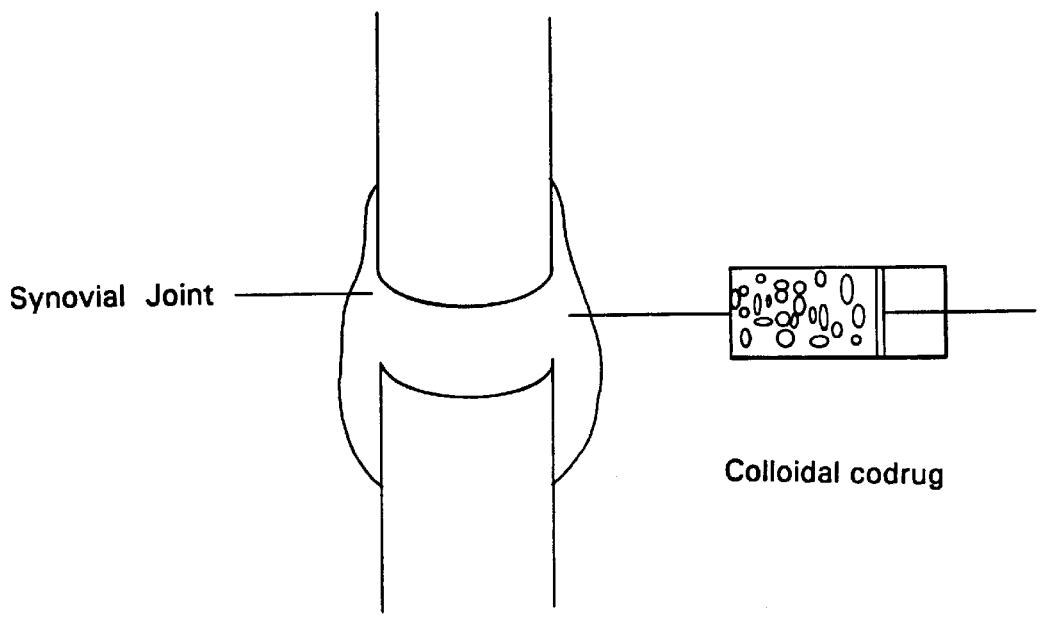
FIG. 5 shows that codrug formulations may be used in the treatment of arthritic conditions by injection into the affected joint.

In another embodiment, a totally bioerodible sustained release system for pharmacologically active agents is composed of codrug alone (either solid, liquid or colloidal). Injectable codrug systems have a variety of applications including, but not limited to arthritis (FIG. 5).

The codrug of the invention may be administered in injectable form selected from the group consisting of liposomes, liquids, suspensions and microsphere nanoparticles. Preparation of such aqueous solutions, liposomes, emulsion and suspensions are known to those of ordinary skill in the art (see *Remington's Pharmaceutical Sciences*, 18th Ed., Mack Publishing Co., Easton, Pa., 1990, pp. 1504–1712, incorporated herein by reference).

Another embodiment of the invention provides a totally bioerodible sustained release system for pharmacologically active agents composed of codrug in a formulation with another bioerodible substance such as polyvinyl acid, polyanyhydride, collagen, or polyalkylcyanoacrylates such as polybutylcyanoacrylate.

Examples of codrugs of the present invention include 5-fluorouracil with corticosteroids, acyclovir with flurbiprofen and timolol (a beta-blocker) with the prostaglandin PGF2-alpha. These codrugs are labile when dissolved in bodily fluids and are rapidly hydrolyzed to regenerate the two active parent drugs. In the solid form however, they are stable, even in an aqueous environment because in order to hydrolyze they must first be in solution.

Pellets of codrugs of the invention, therefore, slowly release drugs in solution or bodily fluids reflecting the low solubility of the conjugated forms. Pellets may be formulated from the codrug compounds alone or with implantable, bioerodible substances may be selected from polylactic acid and polyclycolic compounds. Pellets may be formulated by methods known in the art and may contain 0.1 to about 100% of the codrug composition.

Codrugs may also be formulated in bioerodible or nonbioerodible delivery systems to further control their release. Such bioerodible systems include polylactic acid (bioerodible) to form a film around, or a matrix with a codrug to further improve the pharmaceutical properties. Polylactic acid can be formulated in solutions of 2, 5 and 10% polylactic acid, and has been used to produce 5FU-TRI codrug pellets attached to sutures. 2% polyvinyl alcohol has been used to coat pellets of 5FU-THS for subconjunctival delivery. Polybutyl cyanoacrylate (bioerodible) has been used to form a matrix with 5FU-TRI pellets attached to an intraocular lens haptic and silicone (nonbioerodible) to attach the same pellets to lens haptic (see Example 7 below).

Furthermore, in one embodiment of the invention a pharmacologically active composition possessing some undesirable effects may be conjugated to another agent to reduce the undesirable effects such as isoniazid with pyroxidine. Another embodiment of the invention is a codrug formulated with other drug or prodrug molecules.

Amongst the advantages of codrug systems are that frequently no polymers are required to control release so that the devices can be extremely small (small enough to be fitted onto a haptic of an intraocular lens). Codrugs systems can also be formulated as suspensions (nanoparticle size range) and upper size limitations are only imposed the application method under consideration. There are also no concerns of residual polymer after drug has been released, nor of polymer related toxicity as no polymers are used in the construction of the devices.

Some specific examples of codrugs of the invention are given below:

EXAMPLE 1

Codrug from triamcinolone acetonide and bis (hydroxymethyl)-5-fluorouracil (See scheme 1 below)

Bis(hydroxylmethyl)-5-fluorouracil (2) (158 mg) was dissolved in 5 ml. of acetonitrile in an ice bath. To this stirred solution 112 µL of triethylamine was added followed by triamcinolone acetonide 21-chloroformate (1) prepared from 240 mg of triamcinolone acetonide. The resulting solution was stirred at room temperature overnight, concentrated in vacuo, redissolved in methylene chloride and washed with water and brine. The crude product was chromatographed on silicagel using chloroform-methanol=100:5 as a solvent system, 210 mg of solid codrug 17 was obtained. Yield 61.4%; $^1$H-NMR (CDCl$_3$); δ 0.95 (s,3H C-18), 1.2 (s,3H C-19), 1.4, 1.55 (2s,6H isopropylidene), 3.25 (m, 1H C-16), 4.4 (m, 1H C-11), 4.8 5.15 (2d, 2H C-21), 5.0 (d, 1H OH), 5.7–5.85 (2d, 2H CH$_2$N), 6.15 (s,1H C-4), 6.35 (d,1H C-2), 7.3 (d,1H C-1), 7.65 (d,1H pyrimidyl H-6), 10.0 (s,1H NH).

EXAMPLE 2

Hydrolysis of 5FU/TRI

This example measured the chemical and enzymatic hydrolysis of the 5FU/TRI codrug and determined the release of drug entities.

A stock solution was prepared by dissolving 10 mg of 5FU/TRI in 10 ml acetonitrile. This was then added to a series of phosphate buffers at pH 3, 5, 6.4, 7.4 and 8.4 at 37° C. to give final concentrations of 100 ug/ml. Care was taken to ensure that these solutions were indeed solutions and not suspensions. Samples were periodically removed and assayed by HPLC as described below. Enzymatic hydrolysis was determine in a similar way using pooled serum from 3 volunteers. The assay procedure used distinguished between TRI and 5FU/TRI. 5FU was assayed under different conditions.

HPLC Assays

Samples of buffer containing codrug and hydrolysis products were assayed by HPLC using a fully automated Hitachi system with a C-18 reverse phase column (25 cm×4 mm×5 µm) and uv detection. The mobile phase was 40% acetonitrile buffered to pH 4.0 with 0.02% sodium acetate. The flow rate was 1.0 ml/min and detection was at 238 nm. Under these conditions the retention time of the codrug 5FU/TRI was 17 minutes while triamcinolone acetonide eluted at 9 minutes. Quantitation limits were 0.3 and 0.5 ug/ml, respectively. Under the above conditions 5FU was found to elute with the solvent front and so was assayed separately. For 5FU an Applied Biosystems HPLC system was used with a C-18 reverse phase column (25 cm×4 mm×5 µm) and 0.02% sodium acetate buffer mobile phase (pH 4.0). The flow rate was 1.0 ml/min and detection was by uv at 266 nm. Under these condition the retention time was 6.5 minutes and the detection limit 0.2 ug/ml.

Samples of serum were deproteinated before assay by HPLC. 300 µl serum samples were added to 300 µl acetonitrile in a microcentrifuge tube. After vortex mixing for 10 seconds tubes were centrifuged at 14,000 rpm for 30 minutes. To determine the concentration of codrug and steroid the supernatant was injected directly onto the HPLC (sensitivity to 0.6 ug/ml and 1.0 ug/ml, respectively).

To quantitate 5FU it was necessary to remove acetonitrile before analysis. 300 μl of the supernatant was dried under reduced pressure using a speed vacuum. The dried plug was then rehydrated with 150 μl deionized water before assay by HPLC. Interference from serum residues reduced sensitivity to 1 ug/ml.

The codrug was hydrolyzed in a first-order process to quantitatively generate 5FU and triamcinolone acetonide. The rate of hydrolysis was much faster at high pH and was extremely fast in serum (half-life, $t_{1/2}$, less than 10 minutes).

| pH | $t_{1/2}$ |
|---|---|
| 3.0 | 204 hr |
| 5.0 | 12.7 hr |
| 6.4 | 78 min |
| 7.4 | 14.1 min |
| 8.4 | 9.8 min |
| Serum | 8.8 min |

This example shows that although the 5FU/TRI codrug is stable in acidic conditions, it is highly labile under physiological conditions, breaking down to regenerate 5FU and triamcinolone acetonide.

EXAMPLE 3

5FU/TRI as a Sustained Release System In Vitro

This example measures the release rate of 5FU and triamcinolone from pellets of 5FU/TRI in phosphate buffer.

Pellets (2 mg) of the codrug 5FU/TRI were prepared in a 1.5 mm pellet press using a modified Parr Instrument Press. Pellets were then immersed in 5 ml phosphate buffer (pH 7.4, 37° C.) and 300 μl samples removed each day for 6 days; these were immediately replaced with 300 μl of buffer. Samples were assayed by HPLC for 5FU/TRI, triamcinolone acetonide and 5FU. After 6 days, buffer was completely replaced, to maintain sink conditions, and sampling continued.

No intact codrug was detected in the receptor medium by HPLC (detection limit 0.5 ug/ml). Release of triamcinolone acetonide was found to follow pseudo zero order kinetics with a mean release rate of 1.4+/−0.3 ug/hr. Release of 5FU was found to be 0.4+/−0.06 ug/hr.

These rates were maintained until over 60% of triamcinolone acetonide and 5FU had been released. The mean ratio of 5FU to triamcinolone acetonide concentration (ug/ml) in the receptor solution was 3.40+/−0.15 at all time points, (i.e., equimolar release).

This example demonstrates that codrug delivery systems can be used as sustained release agents however a more thorough in vivo evaluation must be performed.

EXAMPLE 4

5FU/TRI as a Sustained Release System In Vivo

This example measures the release rate and vitreous concentrations of 5FU and TRI from pellets of 5FU/TRI in the rabbit vitreous.

Pellets (2 mg) of the codrug 5FU/TRI were prepared using a 1.5 mm press. These pellets were then fixed onto 6-0 nylon suture using intraocular lens grade silicone. Silicone covered the base of the pellets providing a platform for suture attachment. Alternatively a solution of 2% or 5% polylactic acid was used. Pellets attached by both methods were implanted into the vitreous of 8 New Zealand white rabbits through a small incision through the sclera. For each type of device, two animals were killed after 1, 2, 3, and 4 weeks and the vitreous and aqueous obtained from the frozen sphere. Before death animals were examined with a slit lamp. This platform did not effect release rate (in vitro). Pellets were then implanted into the vitreous of 8 New Zealand White rabbits in a similar manner to that described, except that sclerotomy sites were smaller in this case (2.5 mm). Two animals were sacrificed after 1, 2, 3 and 4 weeks and vitreous and aqueous obtained from the frozen sphere. HPLC analysis was then performed on tissue samples and explanted devices to determine the concentrations of 5FU, triamcinolone acetonide and intact 5FU/TRI.

No intact codrug was detected in the vitreous. Mean intravitreal levels of triamcinolone were found to be 3.0+/−0.9 ug/ml. These levels were maintained for three weeks, declining to 0.8+/−0.4 ug/ml on the fourth week before dropping below the detection limit of the HPLC by week 5.

This experiment shows that sustained levels of TRI and 5FU in the vitreous are achievable by the implantation of a codrug device. Such a device has the advantages of being composed entirely of the required drugs and of being completely bioerodible. No toxic or inflammatory effects are anticipated as the only compounds being released are 5FU, triamcinolone acetonide and formaldehyde.

EXAMPLE 5

5FU-TRI Codrug Implant to Control Scar Formation in Strabismus Surgery

An in vivo evaluation of scar reduction under 5FU-TRI implant after extraocular muscle (EOM) surgery in rabbits, an experimental animal model for correlation to human utility.

In each eye of ten rabbits the inferior rectus muscle (IRM) was disinserted from the globe and electrocautery was used to create a scar between the muscle and sclera. After the IRM was sewn back into its insertion site, four 2 mg codrug implants were inserted between sclera and muscle in the right eye, while the left was used as a control. Bioerodible codrug implants releasing 5FU and TRI over 6 weeks were prepared. Devices release equimolar amounts of 5FU and TRI. Animals were killed at 1, 2 and 3 weeks and eyes eviscerated. Specimens were prepared and stained with H&E. The scar thickness and cellular infiltrate were determined quantitatively using a Bioscan image analysis program.

Drug treated eyes showed an 80% decrease in scar thickness compared to controls (7 to 35 μm). Microscopic examination of a defined area of tissue (40 μm$^2$) revealed a greater number of inflammatory cells present in the control tissue (>300 versus <35). The codrug implant may prove useful in scar reduction following EOM surgery.

EXAMPLE 6

Bioerodible Sustained Release Subconjunctival Co-Delivery of TRI and 5FU

This example determined feasibility of a codrug release system for the subconjunctival co-delivery of 5FU and TRI for possible use in glaucoma filtration surgery.

Figure 2:
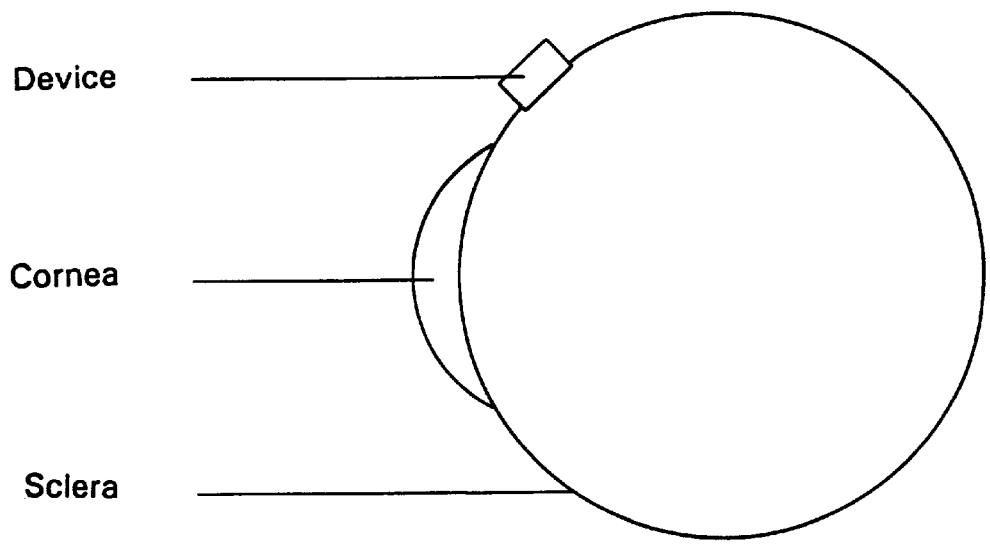
FIG. 2 shows devices were implanted subconjunctivally in each eye of ten rabbits.

Codrug devices were prepared as flat discs 2.5 mm in diameter weighing 5 mg. Each device contained approximately 3.7 mg of TRI and 1.3 mg of 5FU and were composed of over 97% active substance. Devices were implanted subconjunctivally in each eye of ten rabbits (FIG. 2). Toxicity and inflammation were determined by weekly slit lamp examinations and electroretinograms (ERGs). Animals were killed after 3, 7, 10 and 14 days and eyes eviscerated. After freezing at −70° C. devices were removed for determination of residual drugs and the complete vitreous and aqueous dissected from the ice ball to determine the concentration of 5FU and TRI. Two animals were used for histology and were killed 6 weeks after implantation.

Analysis of explanted devices showed 5FU and TRI to have been released at a pseudo zero order rate of 9 +/−1% per day over the first ten days. Devices released equimolar amounts of 5FU and TRI. ERGs were normal for all animals and there was no evidence of toxicity or inflammation around the implantation site.

EXAMPLE 7

Codrugs in the Prevention of Posterior Capsular Opacification

This example investigates the use of codrugs in the inhibition of posterior capsular opacification (PCO) after extracapsular cataract extraction and intraocular lens implantation in the rabbit.

Figure 3:
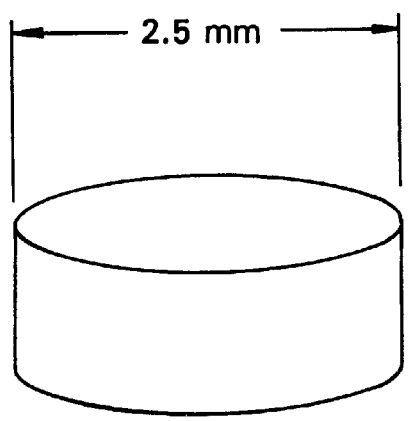
FIG. 3 shows codrug devices are entirely composed of drug and do not require release rate controlling polymers enabling extremely small systems to be prepared. 1.5 mm pellets containing 1.5 mg of triamcinolone acetonide (TRI) and 0.5 mg 5-fluoroaracil (5FU) were small enough to be fixed to the haptics of IOLs.

Codrug pellets were prepared that gave pseudo zero order release of 5FU and TRI in an equimolar ratio over 6 weeks. Codrug devices are entirely composed of drug and do not require release rate controlling polymers enabling extremely small systems to be prepared. 1.5 mm pellets containing 1.5 mg of TRI and 0.5 mg 5FU were prepared and fixed to the haptics of IOLs using the bioerodible polybutyl cyanoacrylate. This polymer is soaked into the pellet forming a codrug/cyanoacrylate matrix as it dried (FIG. 3). 16 New Zealand White rabbits were used in this study, one eye (control) received a polymethyl methacrylate intraocular lens (IOL) (Chiron Intraoptics) while the other received an IOL with codrug. Eyes were examined regularly by slit lamp and PCO scored from 0 to 4+. Retinal function was determined by electroretinogram (ERG) before implantation and before sacrifice. Animals were killed after 4, 8, 12 and 16 weeks; eyes were removed and fixed in formalin. Photographs of posterior capsule were projected onto a grid and the percentage of PCO calculated.

ERG and histopathologic data indicated that the codrugs were well tolerated with no indication of a toxic or inflammatory response. Slit lamp examination showed a statistically significant decrease in PCO between study and control eyes ($p<0.001$). The less subjective assessment of PCO using a grid confirmed this observation and indicated an arrest of opacification in drug eyes with a statistical significance of $p<0.03$ by 8 weeks.

This example indicates that codrug implants are well tolerated in the capsular bag. Significantly, the development of PCO can be controlled over a prolonged period by the use of these implants.

EXAMPLE 8

Intravitreal Co-Delivery of TRI and 5FU

This example evaluates intravitreal co-delivery of 5FU and TRI in an animal model of proliferative vitreoretinopathy (PVR). Previous studies indicate that TRI and 5FU is useful in the treatment of PVR.

Figure 4:
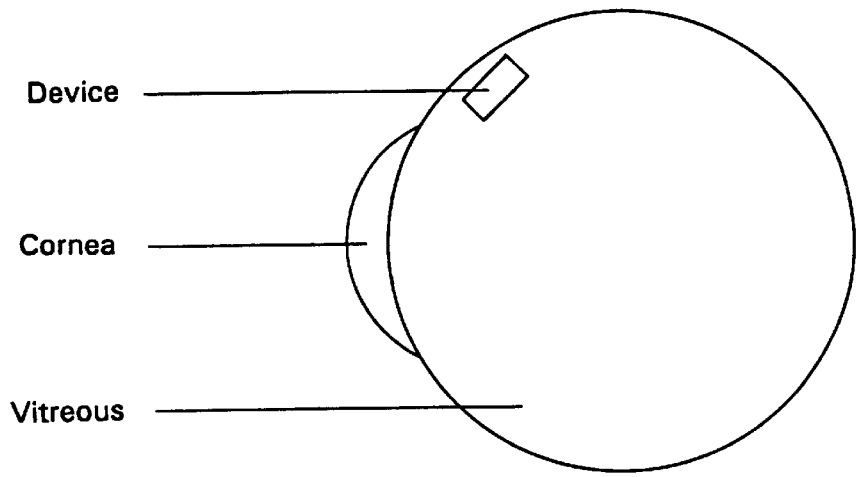
FIG. 4 shows bioerodible codrug implants were prepared 1.5 mm in diameter and attached to 6-0 nylon suture. Implants were immersed in 5 ml of phosphate buffer (pH 7.4) and samples periodically removed for HPLC assay to determine the release of both 5FU and TRI. Implants were then inserted into the vitreous of 14 New Zealand White rabbits.

Bioerodible codrug implants were prepared 1.5 mm in diameter and attached to 6-0 nylon suture. Implants were immersed in 5 ml of phosphate buffer (pH 7.4) and samples periodically removed for HPLC assay to determine the release of both 5FU and TRI. Similar implants were then inserted into the vitreous of 14 New Zealand White rabbits (FIG. 4). Toxicity was assessed by electroretinogram and slit lamp examination in all animals. Histopathologic examination was performed on four animals. Ten animals were used for pharmacokinetics; two animals were killed 1, 2, 3, 4 and 5 weeks after implantation. Eyes were enucleated, devices removed and both vitreous and aqueous obtained. All samples were assayed by HPLC. Five animals received actual devices in one eye and placebo implants in contralateral eyes. These were killed after 3 and 6 weeks for histopathologic examination.

Devices released TRI at 1.4 ug/hr and 5FU at 0.3 $\mu$g/hr in buffer (equimolar release) and were well tolerated in rabbit eyes with no indication of toxicity or inflammation. Vitreous levels of TRI were maintained at 2.4 $\mu$g/ml over the 5 weeks duration of the pharmacokinetic study.

The delivery system described gives pseudo zero order release of both TRI and 5FU in buffer. As the devices are small, they can be readily inserted into a normal scleral MVR blade incision. The devices appear to be well tolerated and maintain high, potentially therapeutic, drug levels in the vitreous. Levels of TRI and 5FU in the aqueous were too low to be detected. Future work will evaluate the use of this codrug system in a PVR model.

EXAMPLE 9

Intravitreal Delivery of an Anti-Neovascular Agent and an Antiproliferative Agent in the Rabbit Eye The example shows codrug technology as a means to achieve the intravitreal delivery of $3\alpha$, $17\alpha$, 21-trihydroxy 5$\beta$ pregnane-20-one (THS), a model angiogenesis inhibiting steroid, and 5FU. THS has no corticosteroid activity but inhibits neovacularization in the chick embryo and rabbit cornea models. Activity of this and related agents can be enhanced by a variety of agents including aurin tricarboxylic acid, and cyclodextran.

Other workers have reported that antimetabolites can also inhibit neovascularization. Increased efficacy of THS may be anticipated from the coadministration of 5FU. The inventors have developed a bioerodible implantable device by preparing a 5FU/THS codrug. In vitro, devices release 2 moles of 5FU for each mole of THS.

2 mg codrug devices were implanted into the vitreous of 20 New Zealand White rabbit eyes (ten animals) through 2.5 mm incisions parallel to and 3 mm from the limbus. Animals were also examined by slit lamp and retinal function was assessed by electroretinogram (ERG) examination before implantation and immediately before sacrifice. Animals were periodically killed after implantation and eyes immediately enucleated and frozen. Vitreous was then assayed for 5FU, THS and intact codrug by HPLC. Explanted devices were also assayed for residual drug.

Proliferative Vitreoretinopathy

To treat proliferative disorders in the vitreous or lens capsule such as proliferative vitreoretinopathy or posterior capsular opacification therapeutic concentrations of 5FU (over 0.5 ug/ml) and corticosteroid (1 ug/ml) should be maintained so as to at the same time inhibit fibroblast proliferation (5FU inhibits growth of fibroblasts) and prevent inflammation which stimulates their proliferation (TRI has potent anti-inflammatory properties).

Method to achieve sustained release of two or more Pharmacologically active compounds or codrugs from an injectable formulation.

A 10 mg/ml suspension of 5FU-TRI codrug was prepared in isotonic phosphate buffer. This was injected into the vitreous of 3 rabbits. One animal was killed after 1, 3 and 7 days and both eyes were removed. HPLC analysis was performed on each eye to detect intact codrug, TRI and 5FU. Injection of the suspension was found to maintain therapeutic levels of both 5FU and TRI in the vitreous over the 7 day duration of this study.

EXAMPLE 10

A 5FU/TRI codrug conjugate according to the invention was found to be unstable in buffer at pH 7.4, although it was stable in pH 3.0 (respective $t_{1/2}$ less than 15 minutes and over 5 days).

The compound is moreover relatively insoluble so that a pellet can be compressed that does not dissolve in buffer at pH 7.4. Such a pellet slowly releases both TRI and 5FU over an extended period of time (months) even when immersed in pH 7.4. The advantage of such a system is that although each of the parent compounds are released, the intact conjugate is never detected in solution (its half-life is too short). This conjugate can be formulated into a totally bio-erodible sustained release system for 5FU and triamcinolone in the eye. Both agents are presently used in combination and a sustained release form for one or the other has been a goal of ophthalmologists for a long period.

In a similar way a conjugate of 5FU and TRI can be used as a codrug compound for the treatment of proliferative vitreoretinopathy (PVR). A pellet of such an implant with similar properties to the above is implanted intravitreally after vitrectomy and is found to reduce the occurrence of PVR. Animal studies are proceeding.

An additional manifestation of the codrug idea is the conjugation of an anti-viral compound (ganciclovir or acyclovir) with a nonsteroidal anti-inflammatory agent (flurbiprofen or indomethacin). These conjugates are insoluble and would be suitable for subconjunctival implantation in herpes keratitis.

EXAMPLE 11

The following is the structure of 5FU linked via a carbonate bond to a glycerol diflurbiprofen ester. The rationale is that the compound would hydrolyze in vivo to release 5FU, glycerol and two molecules of flurbiprofen.

EXAMPLE 12

Codrug from Flurbiprofen and Acyclovir (See Scheme 2 Below)

200 mg of acyclovir, 160 mg of flurbiprofen, 200 mg of dicyclohexylcarbodiimide (DCC) and 13 mg of dimethylaminopyridine (DMAP) were mixed with 7 ml of dimethylformamide. The mixture was stirred at 55° C. overnight, then evaporated to dryness under vacuum. The solid residue was chromatographed on silicagel to yield 340 mg of the codrug (3a). $^1$H-NMR (DMSO), δ 1.4 (d, 2H CH$_2$O), 3.8 (q, 1H CH), 4.1 (m, 2H), 5.3 (s,2H NCH$_2$O), 6.5 (s, 2H NH$_2$), 7.15–7.55 (m,8H arom.), 7.8 (s, 1H CH).

EXAMPLE 13

Codrugs from bis(hydroxymethyl)-5-fluorouracil and flurbiprofen (See scheme 3 below)

Flurbiprofen acid chloride (282 mg) was dissolved in 3 ml of acetonitrile. To this stirred solution triethylamine (142 mg) was added followed by 5-fluorouracil (2) derivative (170 mg). The cloudy mixture was stirred at room temperature overnight, diluted with dichloromethane, then washed with aqueous NaHCO$_3$ solution, water and brine. Chromatography on silica gel yielded 2 codrugs (4a). 145 mg of monosubstituted product and 160 mg of bissubstituted product. $^1$H-NMR (acetone) for monoester, δ 1.7 (d,3H CH$_3$), 3.9 (q, 1H CH), 5.75 (s,2H CH$_2$N), 7.2–7.6 (m,8H arom.), 7.92 (d,1H). $^1$H-NMR (acetone) for diester, δ 1.5 (m, 6H 2CH$_3$), 3.75 (m, 2H 2CH), 5.6 (s,2H CH$_2$N), 6.0 (s, 2H CH$_2$N), 7.0–7.6 (m,16H arom.).

EXAMPLE 14

Codrug from Prostaglandin PGF$_{2\alpha}$ and Timolol 102 mg of protected prostaglandin PGF$_{2\alpha}$ was dissolved in 4.5 ml of methylene chloride at 0° C. To this solution carbonyldiimidazole (35 mg) was added and the resulting solution was stirred at 0° C. for 40 min. The solution of timolol (54 mg) in 1 ml of methylene chloride was then added and the mixture was heated at 50–54° C. overnight. The solution was washed with water and brine. Thus obtained crude product was purified by chromatography and redissolved in tetrahydrofuran (3 ml) at 0° C. To this stirred solution tetrabutylammonium fluoride was added. After 0.5 h the solvent was evaporated, the residue was dissolved in ethyl acetate, washed with dil. sodium bicarbonate solution, brine and dried over Na$_2$SO$_4$. The oily residue was purified by preparative TLC to yield the expected codrug (39% of yield). $^1$H-NMR (CDCl$_3$), δ 0.85 (t, 3F CH$_3$), 1.1 (s, 9H t-Bu), 2.56 (d,2H CH$_2$N), 3.5 (m,4H), 3.8 (m,4H), 3.9–4.2 (m,4H 3CHO+OH), 4.6 (m, 2H CH$_2$O), 5.25 (m, 1H CH—O), 5.3–5.6 (m, 4H olefine).

Synthesis Scheme

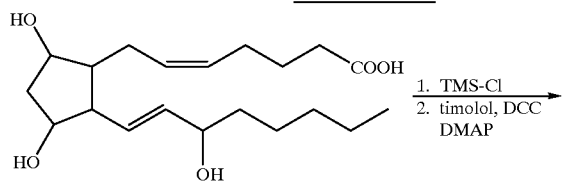

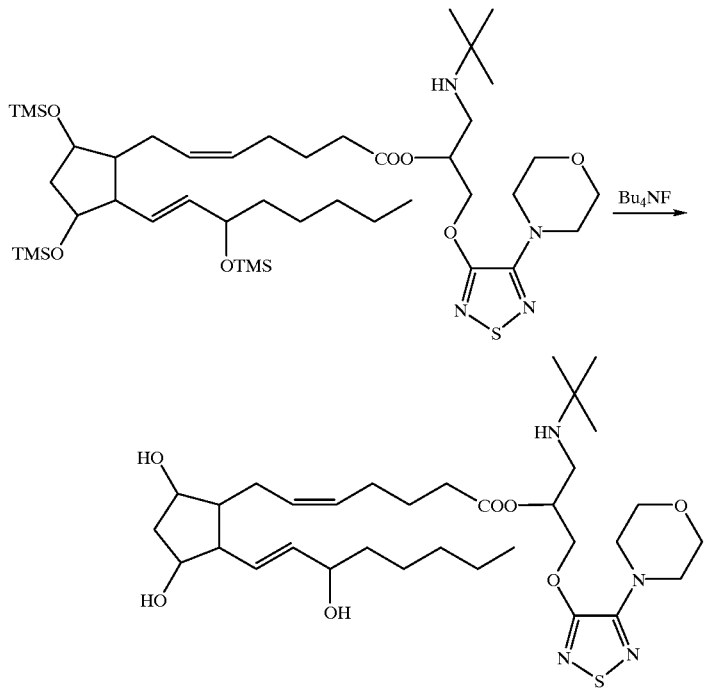

EXAMPLE 15

Codrug made of 5β-pregnane-3α, 17α, 21-triol-20-one, flurbiprofen and 5-fluorouracil (scheme 4)

1.4 ml of the solution of phosgene in toluene and 1 ml of the THF were cooled to 0° C. in an ice-bath. To this stirred mixture the solution of (5) (60 mg) and triethylamine (14.5 μL) in 1.5 ml of THF was slowly added. After 6 h the excess of phosgene and the solvent were removed in a stream of nitrogen. The residue was diluted with 1 ml of acetonitrile and the solution of bis(hydroxymethyl) -5-fluorouracil (2) (50 mg) and triethylamine (29 μL) in 1.5 ml of acetonitrile was added. The resulting homogenous solution was kept in refrigerator overnight. The residue obtained after solvent evaporation was purified by preparative TLC yielding 52 mg of the codrug (6). $^1$H-NMR (CDCl$_3$), δ 0.6 (s, 3H C-18), 0.9 (s,3H C19), 1.52 (d,3H CH$_3$), 3.7 (q,1H CH), 4.75 (m,1H C-3), 4.8–5.3 (2d,2H C-21), 5.7 (s,2H CH$_2$N), 7.1–7.55 (m,8H arom.), 7.6 (d, 1H CH).

EXAMPLE 16

Esters of acyclovir with flurbiprofen and indomethacin have been synthesized as shown in Scheme 2 set forth below, from the corresponding acids (activated with N,N-dicyclohexylcarbodiimide). Using this method the ester of flurbiprofen 3a has been readily obtained, but when indomethacin was used the amidoester 3b surprisingly was isolated from the reaction mixture.

The conjugate of ganciclovir and indomethacin has been synthesized as presented in Scheme 5. This diester could not be obtained by simple esterification. However, when the primary amino group was protected as an N-trityl derivative 7 (via the intermediate diactetate), the acylation with excess of indomethacin acid chloride gave the expected diester 8.

Synthesis of the monoester of ganciclovir with flurbiprofen, Scheme 6, required selective protection of one of the two primary hydroxyl groups in ganciclovir 9. This was achieved by treating the latter with 2.5 eq. of monomethoxytrityl chloride in the presence of triethylamine and DMAP. The resulting ditrityl derivative 10 was treated with flurbiprofen acid chloride to give the fully protected monoester 11. Removal of the trityl groups with acetic acid provided the desired codrug 12.

EXAMPLE 17

Conjugates of 5-fluorouracil with flurbiprofen, indomethacin, and triamcinolone acetonide.

5FU remains a clinically important antiviral and antitumor agent, but it possesses high toxicity and far from optimal delivery properties. Synthesis of a series of 5FU conjugates with anti-inflammatory drugs such as flurbiprofen, indomethacin, and triamcinolone acetonide resulted in compositions with improved properties.

5FU can be attached to hydroxy compounds as carbamate (via the intermediate chloroformate) as shown in Scheme 7 below.

In the case of menthol 13, the stable product has been obtained. If, however, an oxygen atom is introduced at the proximity of the hydroxyl group, the carbamate bond becomes very labile. Via NMR, the inventors were able to prove a carbamate bond was formed. An attempt to prepare the carbamate from 5FU and triamcinolone acetonide-21-chloroformate 1 failed completely. The inventors investigated the esterification of the known 1,3-bis-(hydroxymethyl)-5FU 2 with acid chlorides and chloroformate. Compound 2 has been obtained from 5FU and formalin as a viscous oil containing ca. 60% of the bis-(hydroxymethyl) derivative and ca. 35% of both the isomeric mono-(hydroxymethyl) products. This mixture was used in all subsequent reactions without further purification.

Flurbiprofen and indomethacin acid chlorides were coupled with 2 in acetonitrile in the presence of triethylamine to give a mixture of the mono and diesters (Scheme 3).

In both cases the major product was the 1-substituted derivative and the separation of the mixture did not present any difficulty.

An alternative approach involved the use of hydroxyesters of flurbiprofen to attach the 1,3-bis-(hydroxymethyl)-5FU via a carbonate link (Schemes 8 and 9).

In the scheme 8 example, the monoester of flurbiprofen and triethylene glycol 13 was prepared. the synthesis required selective protection of one of the two hydroxyl groups as a silyl derivative. Subsequent acylation and deprotection led to the expected monoalcohol. This product was chloroformylated in THF with a solution of phosgene, and coupled with 2 to yield the desired codrug 14.

Alternatively, flurbiprofen 1,3-diglyceride 15 was obtained by the methods of Scheme 9. In the first approach, dihydroxyacetone was readily acylated with flurbiprofen acid chloride in the presence of pyridine, and the central keto group was rapidly reduced by sodium borohydride in THF solution. A purification procedure using column chromatography on silica gel led to the expected monoalcohol 14.

The second approach involved the preparation of 1,3-benzylidene glycerol, protection of the remaining hydroxyl group as an O-benzyl derivative, acidic hydrolysis of the acetal and acylation of the diol with flurbiprofen acid chloride. Finally the benzyl group was removed by transfer hydrogenation in the presence of 10% Pd/C. Compound 15 was chloroformylated and coupled with the 5-fluorouracil derivative as described above, to yield the desired codrug 16.

Triamcinolone acetonide was bonded to the 1,3,-bis-(hydroxymethyl)-5FU 2 via a carbonate (Scheme 1) linkage. The product, obtained after the treatment of TRI with phosgene, contained only one chlorformyl group. Steric considerations make it practically impossible for the reaction to occur with the 11β-hydroxyl group. The monochloroformate obtained above was coupled with 2 to give the expected crystalline codrug 17 after chromatographic purification.

EXAMPLE 18

Codrugs Based on 5β-Pregnane-3α,17α,21-Triol-20-One.

Triple codrugs composed of 3 components including an antimetabolite agent (5FU), and anti-inflammatory agent (flurbiprofen) and an antivasculating agent (5β-pregnane-3α,17α,21-triol-20-one).

Initially, two model compounds 19 and 20 (Schemes 10 and 11) were synthesized and evaluated with respect to the stability in aqueous solution as a function of pH.

The easily available 5β-androgen-3α-ol-17-one (18) was acylated with flurbiprofen acid chloride in pyridine in the presence of DMAP. The resulting ketoester 19 was then reduced in high yield to the alcohol 20. For the completion of the synthesis, the alcohol was chloroformylated in the usual fashion, and coupled with 5FU to yield the expected product 21.

In the second synthesis model, the simple ester 22 of flurbiprofen and 5β-pregnane-3α,17α,21-triol-3,20-dione was obtained as shown in Scheme 11. Synthesis of all "triple" codrugs have been based on the easily available and relatively cheap Reichstein's Substance 23 (Scheme 4). This material was transformed in the usual way (formalin and concentrated HCl in methylene chloride) to its bismethylenedioxy derivative, which was then hydrogenated in high yield with palladium-on-calcium carbonate in the presence of potassium hydroxide, to the saturated 5β-pregnanone. This ketone was then reduced with sodium borohydride, predominantly to the equatorial alcohol 24; the axial alcohol was obtained as a minor side product. The acylation of 24 with flurbiprofen acid chloride yielded the ester 25. For the completion of the synthesis, the dihydroxyacetone side chain was liberated by treatment of 25 with hydrofluoric acid in THF, and the resulting diol 5 was chloroformylated and coupled with 2 to give the desired codrug 6.

The synthesis of the next series of codrugs is shown in Scheme 12. The hydroxyl group of the alcohol 24 was protected as an O-benzyl derivative and then the bismethylenedioxy group was hydrolyzed in the usual fashion. The selective acylation of the 21-hydroxy group led to the flurbiprofen ester 26. The benzyl group was removed by transfer hydrogenation and the resulting alcohol was converted to the chloroformate 27. This product was then subject to coupling with either 1,3-bis-(hydroxymethyl)-5FU, 2, or 5FU itself, which gave the corresponding codrugs 28 and 29, respectively. Independently the two codrugs containing only 5FU and 5β-pregnane-3α,17α,21-triol-20-one were prepared (Scheme 13).

The alcohol 24 was hydrolyzed an(d chloroformylated to the bis-chloroformate 30. When compound 30 was coupled with a 3 equivalents excess of 2, the expected codrug 31, containing two 5FU residues, was obtained. However, if only a 1.5 equivalents excess of 2 was used, the monocarbonate 32 was isolated. The structure of 32 was proven by $^1$H and $^{13}$C NMR analysis.

Due to the remarkable stability of flurbiprofen esters at pH 7.4, an alternative type of linear unit between flurbiprofen and the steroidal alcohols was considered (Scheme 14).

In the reaction of chloroformate 33 with the salt of flurbiprofen, it was expected that a mixed anhydride of flurbiprofen and carbonic acid would be obtained. Instead, however, the ester 34 was isolated as the only product. Obviously, 34 is formed from the unstable, intermediate mixed anhydride by elimination of carbon dioxide.

EXAMPLE 19

Derivatives of Acetazolamide

Acetazolamide is a useful drug for the treatment of glaucoma. However, due to its unfavorable lipophilicity it is not active when given topically to the eye. Approaches to solve the delivery problems may include the development of appropriate codrug forms. Preparation of sulfocarbamate derivatives of acetazolamide are shown in Scheme 15. The product 35 appears to stable in buffer solution to ensure a sufficient rate and extent of codrug conversion to the parent drug at this time.

EXAMPLE 20

The following example relates to a method for making and using a suramin and amiloride codrug as a means to inhibit angiogenesis. It is well settled that individually both suramin and amiloride are potential therapies for angiogenesis and cancer.

Specifically, Vassalli and Belin, FEBS Letters, "Amiloride Selectively Inhibits the Urokinase-type Plasminogen Activator" Volume 214, Number 1, p. 187–191 (April 1987), describe the selective inhibition of urokinase-type plasminogen activator by amiloride in cell culture. Kellen et al., "Antimetastatic Effect of Amiloride in an Animal Tumour Model", Anticancer Res., Volume 8, p. 1373–1376 (1988) show that amiloride exerts an anti-metastatic effect in a rat model. The anti-angiogenic effects of amiloride have been demonstrated in the embryonic egg model (CAM assay) by Chen et al., Investigative Ophthalmology and Visual Science, Vol. 35, No. 4, Abstract 1157-28, Mar. 15, 1994. The same authors have presented data showing a beneficial effect of systemically administered amiloride on subretinal neovascularization in man (Chen et al., Investigative Ophthalmology and Visual Science, Vol. 35, No. 4, Abstract 1171-42, Mar. 15, 1994).

Suramin, which inhibits various growth factors, has been shown to retard wound healing when applied in a liposomal form (Butler et al., Investigative Ophthalmology and Visual Science, Vol. 35, No. 4, Abstract 829-86, Mar. 15, 1994). Collins et al., "Inhibition of Angiogenesis by Suramin", Cancer Research, Volume 52, p. 5073–5075 (Sep. 15, 1992) and Hassan et al., Investigative Ophthalmology and Visual Science, Vol. 35, No. 4, Abstract 566-14, Mar. 15, 1994), have also shown suramin to be a potent inhibitor of angiogenesis in the Chick Chorioallantoic Membrane (CAM) assay. See also Abstracts 417, Amiloride; and 8696, Suramin Merck Index, 11th Ed., Merck and Co., Inc. (1989) and references cited therein, incorporated by reference herein in its entirety.

The chemical structures of amiloride and suramin are set forth below.

amount to inhibit angiogenesis of a codrug of suramin ionically linked to amiloride to a patient in need of angiogenesis inhibition.

Effective dosages of suramin-amiloride codrug are in the range of about 1–30 mg/kg body weight and preferably from about 10–20 mg/kg body weight.. The suramin/amiloride codrug is preferably formulated into a sustained release pellet comprising about ½ gram of codrug. The suramin/amiloride codrug may be formulated for ophthalmic use to achieve an effective concentration in the eye of 5 mcg/ml of codrug components, in a liquid formulation. In the alternative, the codrug may be administered intra-arterially for the treatment of Kaposi's sarcoma. The suramin/amiloride codrug may be administered by injection for the treatment of arthritis.

EXAMPLE 21

Codrug from Ethacrynic Acid and Atenolol

Ethacrynic acid is a diuretic and atenolol is an antihypertensive drug. They may be formulated into a codrug as follows. 200 mg of ethacrynic acid was dissolved in 4 mL of

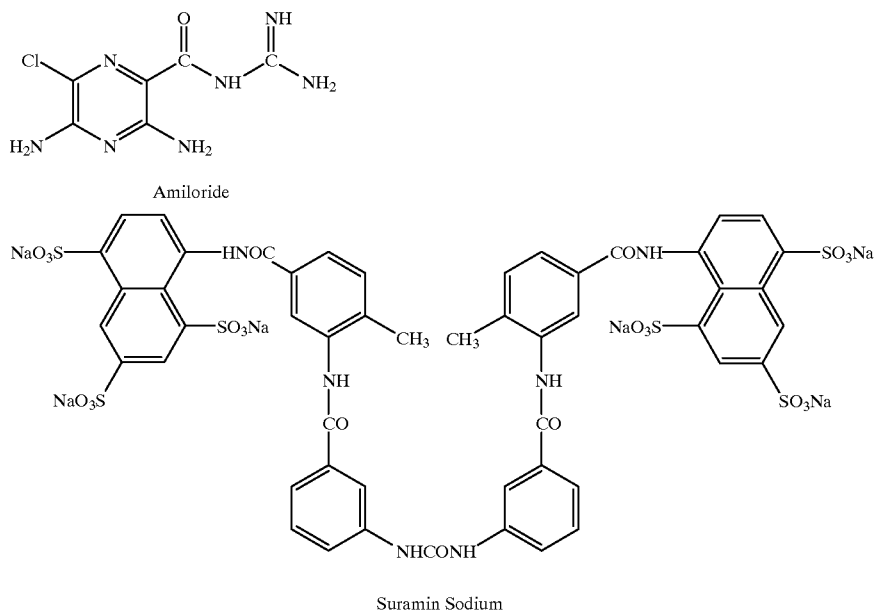

anhydrous dichloromethane and to this stirred solution at room temperature 128 mg of DCC was added followed by 10 mg of dimethylaminopyridine (DMAP) and 128 mg of atenolol. The resulting mixture was stirred at room temperature overnight, diluted with 30 mL of dichloromethane, washed with sodium bicarbonate solution, water and brine. The residue after solvent evaporation was chromatographed on silicagel to yield 62 mg of the expected codrug. $^1$H-NMR (CDCl$_3$) δ 1.14 (t, 3H), 1.26 (d, 3H), 1.31 (d, 3H), 2.46 (q, 2H), 3.50 (s, 2H), 3.52 (m, 1H), 4.25 (m, 1H), 4.91 (2d, 2H), 5.60 (s, 1H), 5.94 (s, 1H), 7.12–7.28 (m, 6H). See synthesis sheme 16 below.

EXAMPLE 22

Codrug from THS, 5-FU and Diethylene Glycol

3α,17α-21-trihydroxy-5β pregnane-20-one (THS) can be formulated in to a codrug with 5FU and diethylene glycol to These reports show that although both suramin and amiloride individually inhibit angiogenesis, their mode of action is different. Thus, the two agents administered linked together by ionic bonding as a codrug appear to have a synergistic effect.

Amiloride is available from Sigma Chemical Co., St. Louis Mo. and Suramin is available from Mobay Chemical Co, New York, N.Y. The two drugs are ionically linked to one another via an ionic bond to form a single codrug salt compound.

The two drugs may be ionically linked by mixing solutions of the two compounds. Amiloride is dissolved in water to form a saturated solution. Suramin is added to the amiloride solution and suramin/amiloride salt forms. Six amiloride molecules ionically bond to each single suramin molecule. The precipitate is collected.

A method of inhibiting angiogenesis according to the present invention comprises administering an effective form an angiostatic steroid. A biscarbonate of THS and diethylene glycol (75.3 mg) was chloroformylated with phosgene in tetrahydrofuran in the presence of triethylamine. Thus obtained bischloroformate was dissolved in dry acetonitrile and conjugated with bishydroxymethyl-5-fluorouracil. The column chromatography on silicagel afforded 95 mg of codrug (79% yield) as a white solid foam. $^1$H-NMR (CDCl$_3$) δ 0.64 (s, 3H, C-18), 0.92 (s, 3H, C-19), 3.73 (m, 8H, PEG), 4.22–4.38 (m, 8H, PEG), 4.59 (m, 1H, C-3), 5.20 (dd, 2H, C-21), 5.70 (m, 4H, 2×OCH$_2$N), 7.68, 7.70 (2d, 2×CH═CF), 9.72, 9.83 (2d, 2H, NH) ppm; $^{13}$C-NMR (CDCl$_3$) δ 205.0 (C-20), 157.2, 156.9 (2d, 2×C-4'), 154.9, 154.7, 154.6, 154.5 (4×OCOO), 149.3, 149.2 (2×C-2'), 140.2 (d, C-F), 128.4 (d, C-6'), 90.4 (C-17), 78.3 (C-3), 23.1 (C-19), 14.7 (C-18) ppm. See synthesis sheme 17 below.

EXAMPLE 23

Codrugs from THS, 5FU and Tetraethylene Glycol

3α,17α-21-trihydroxy-5β pregnane-20-one (THS) can be formulated in to a codrug with 5FU and tetraethylene glycol to form an angiostatic steroid. 112.9 mg of the prodrug prepared from THS and tetraethylene glycol was dissolved in 3 mL of dry THF and triethylamine (55 μL) was added followed by the solution of phosgene (2.81 mL). The mixture was stirred at room temperature overnight, evaporated to dryness, redissolved in dry acetonitrile (2 mL) and added to the stirred solution of bishydroxymethyl-5-fluorouracil (150 mg) and triethylamine (66.3 μL) in acetonitrile (5 mL). After 14 hours at room temperature the products were isolated and purified by column chromatography affording the two codrugs: more polar 15 (129.3 mg, 69% yield) and less polar 16 (20.7 mg, 14% yield), both as white solid foams. 15 $^1$H-NMR (CDCl$_3$) δ 0.62 (s, 3H, C-18), 0.95 (s, 3H, C-19), 3.64–3.78 (m, 12H, PEG), 4.29–4.37 (m, 4H, 2×OCOOCH$_2$), 4.63 (m, 1H, C-3), 5.00(dd, 2H, C-21), 5.65, 5.67 (2s, 4H, 2×NCH$_2$O), 7.65 (2d, 2H, CH═CF), 9.25, 9.35 (2×NH) ppm; $^{13}$C-NMR (CDCl$_3$) δ 205.0 (C-20), 154.9, 154.6, 154.1 (3×OCOO), 90.1 (C-17), 80.0 (C-3), 23.1 (C-19), 14.6 (C-18) ppm. 16 $^1$H-NMR (CDCl$_3$) δ 0.66 (s, 3H, C-18), 0.94 (s, 3H, C-19), 3.61–3.79 (m, 14H, OCH$_2$-PEG), 4.30–4.34 (m, 2H, OCOOCH$_2$), 4.64 (m, 1H, C-3), 4.98 (dd, 2H, C-21), 5.65 (s, 2H, OCH$_2$N), 7.62 (d, C6'), E.70 (1H, NH) ppm; $^{13}$C-NMR (CDCl$_3$) δ 204.5 (C-20), 156.2 (d, C-4'), 154.9, 154.2 (2×OCOO), 148.7 (C-2'), 140.1 (d, C-F), 128.1 (d, C-6'), 90.2 (C-17), 80.0 (C-3), 72.3 (OCOO$\underline{C}$H$_2$) 71.4 (OCH$_2$N), 67.6 (CH$_2$OH), 23.1 (C-19), 14.7 (C-18) ppm. See synthesis sheme 18 below.

EXAMPLE 24

Codrug from PG-F$_{2\alpha}$ Triacetate and Timolol

Prostaglandin F2 alpha (PGF2α) can be formulated into a codrug with timolol (TM) as set forth below. PG-F$_{2\alpha}$ triacetate (95.4 mg) was dissolved in 3 mL of dry dichloromethane and DCC (41.2 mg) was added followed by dimethylaminopyridine (10 mg). The mixture was stirred at room temperature for 15 min. and the solution of timolol (119.6 mg) in 1 mL of dichloromethane was added.

The resulting mixture was stirred at room temperature overnight, filtered, diluted with dichloromethane, washed with water, brine and finally dried over sodium sulfate. The residue after solvent evaporation was separated by column chromatography affording the codrug (61.3 mg, 39.7% yield) as an oil. $^1$H-NMR (CDCl$_3$), δ 0.88 (t, 3H), 1.07 (s, 9H), 1.24–1.7 (m, 14H), 2.02 (s, 3H), 2.04 (s, 3H), 2.05 (s, 3H), 2.30 (m, 2H), 2.54 (m, 2H), 2.80 (d, 2H), 3.50 (m, 4H), 3.78 (t, 4H), 4.58 (m, 2H), 4.88 (m, 1H), 5.08 (t, 1H), 5.23 (m, 2H), 5.34 (m, 2H), 5.53 (m, 2H) ppm. See synthesis sheme 19 below.

Dosages may be calculated by those of skill in the art in accordance with methods set forth in Goodman and Gilman, *The Pharmacological Basis of Therapeutics,* 8th Ed., Pergamon Press, NY, 1990; and *The Merck Index,* 11th Ed., Merck and Co., Inc., Rahway, N.J. 1989; incorporated herein by reference in their entireties. Dosages are preferably in the range of about 1 to about 500 mg/kg body weight, and are administered preferably 1 to 2 times a day.

SCHEME 1

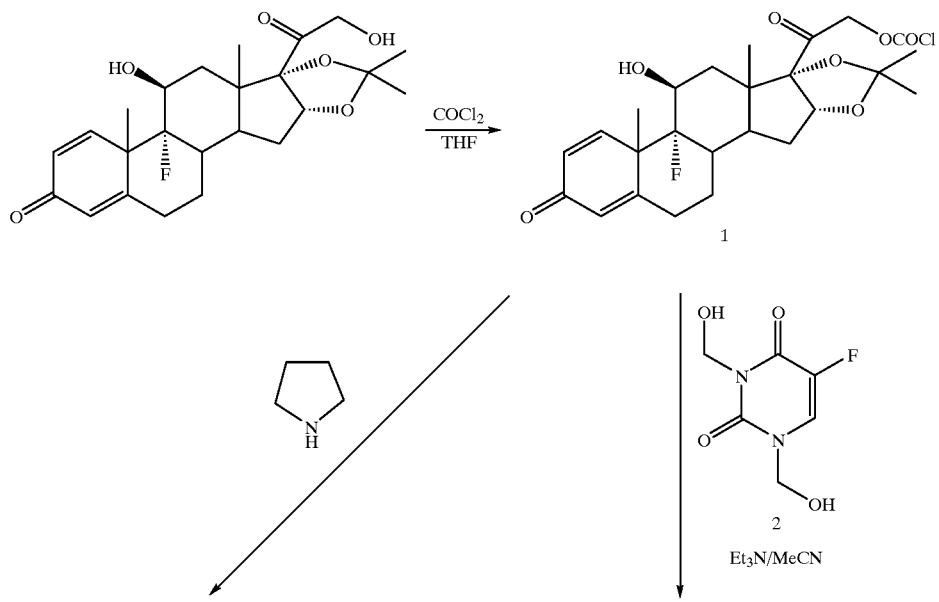

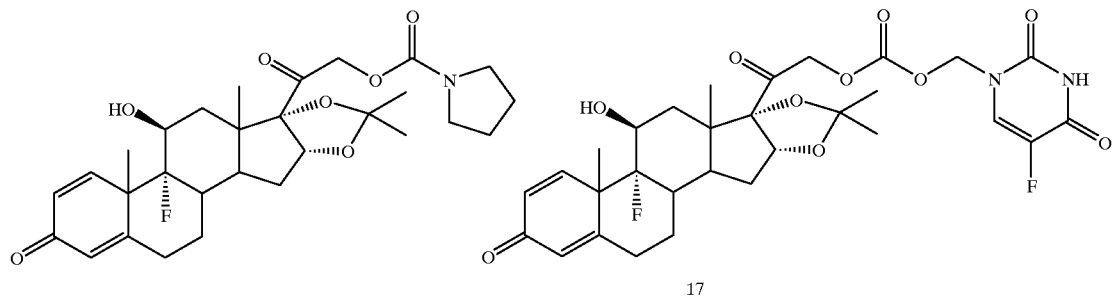
SCHEME 2
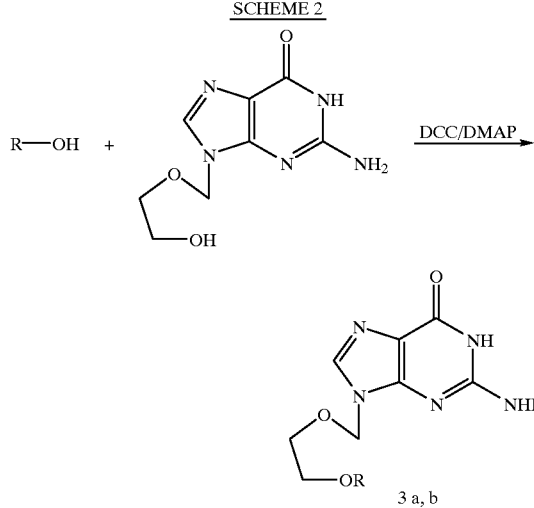
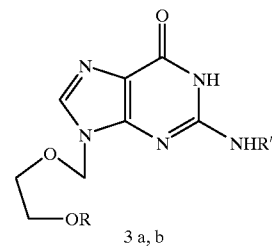
SCHEME 3
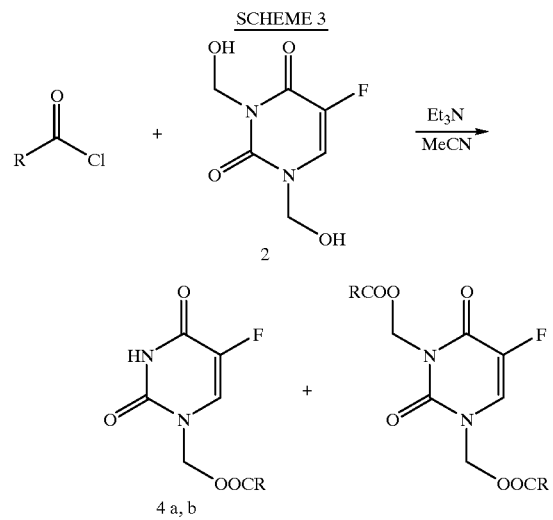
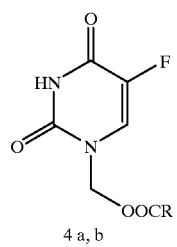
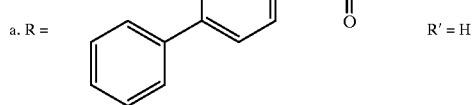
a. R =
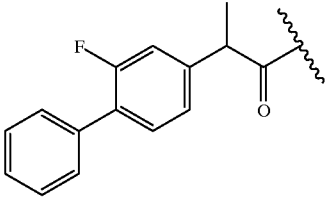
a. R =
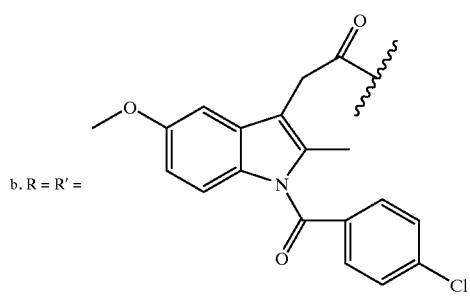
b. R = R' =
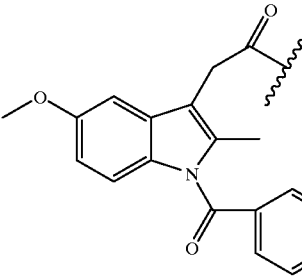
b. R =

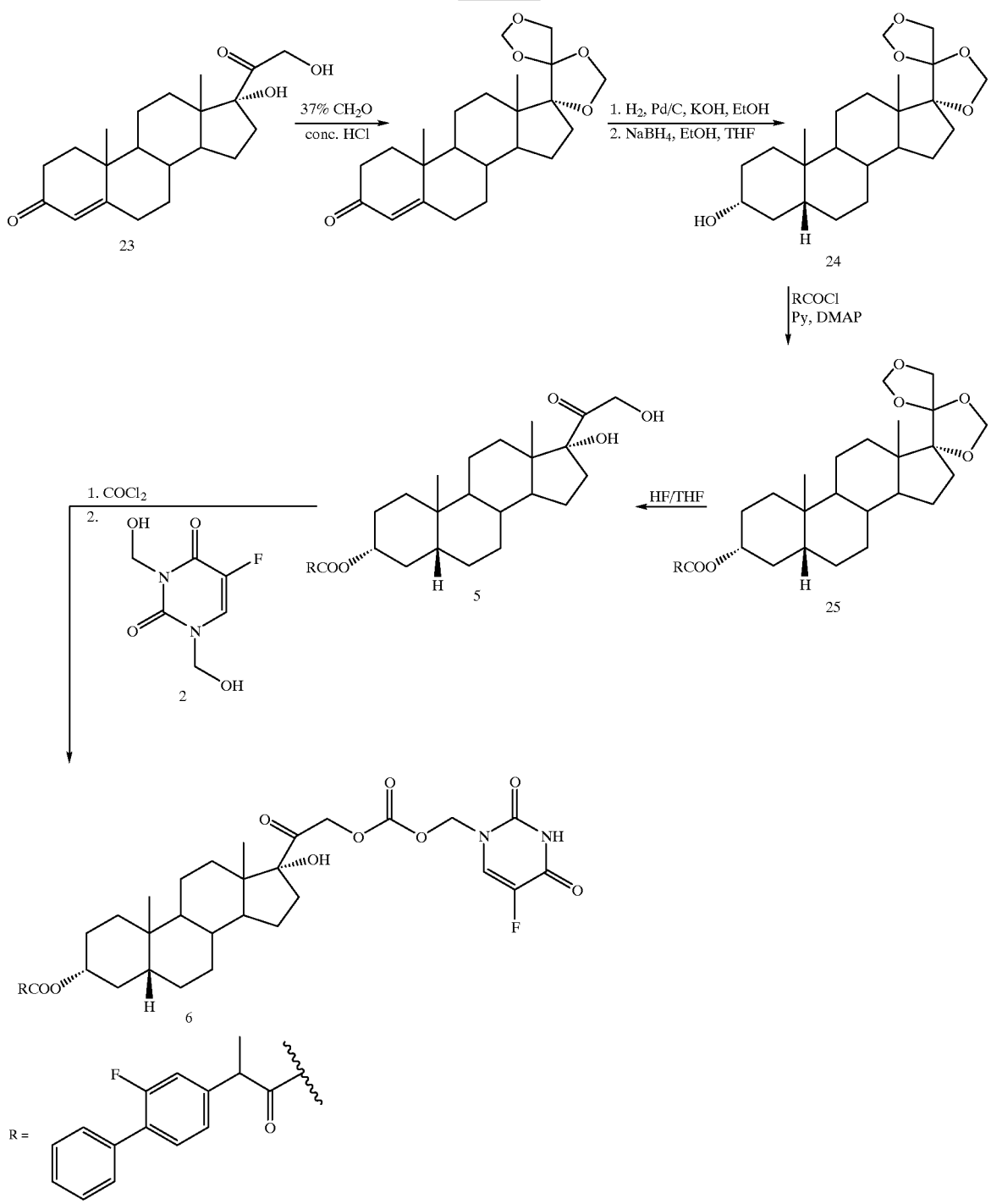

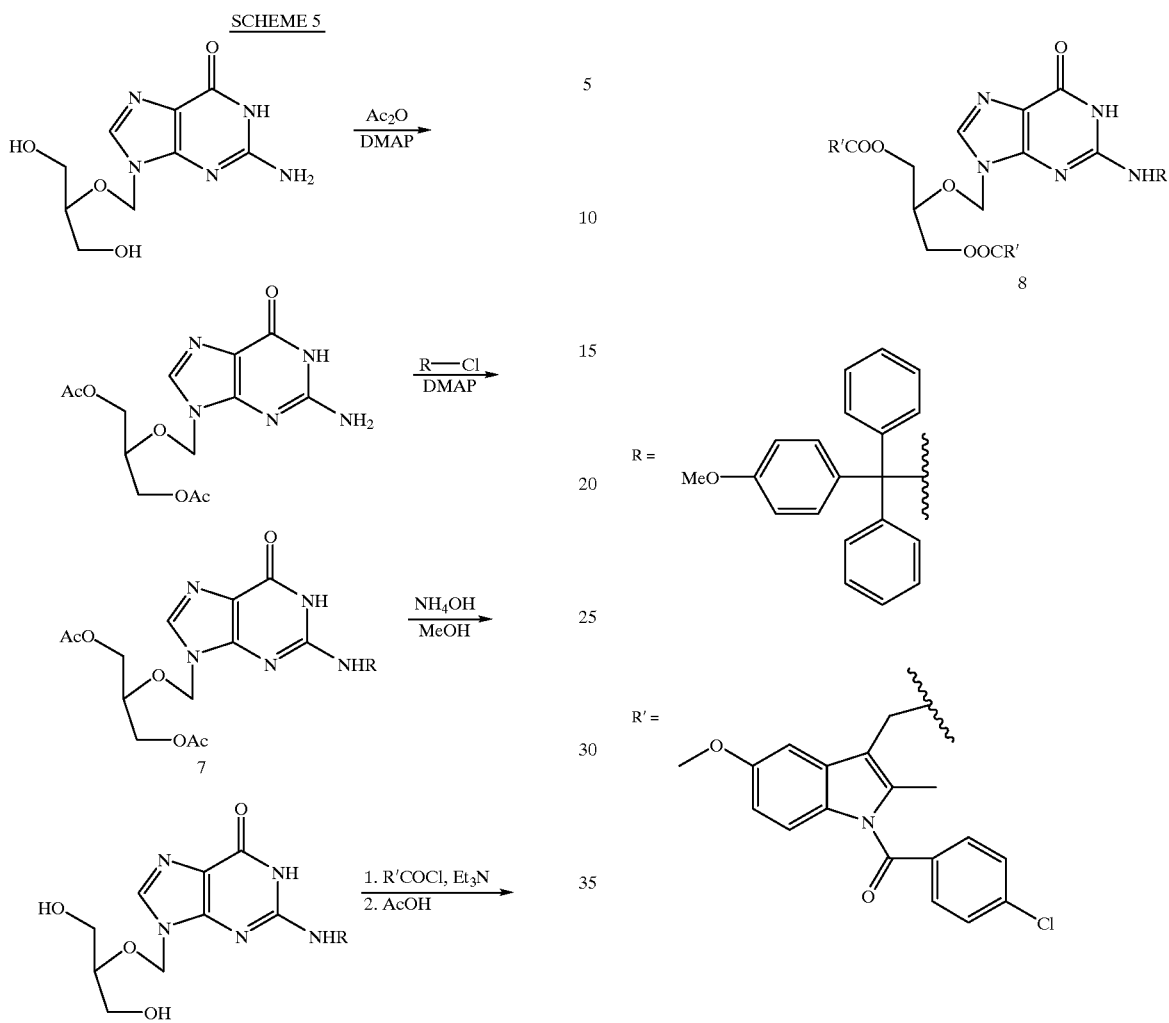
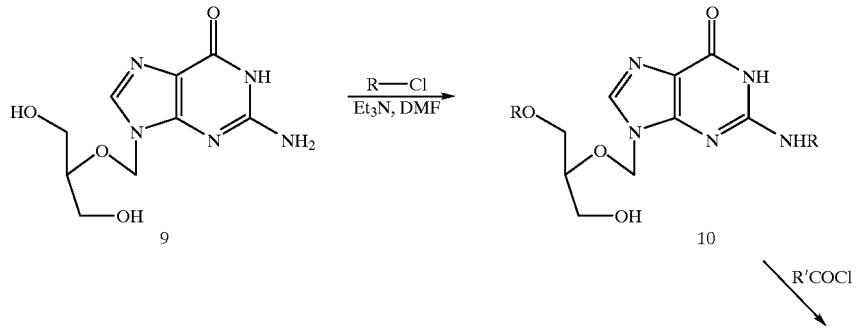

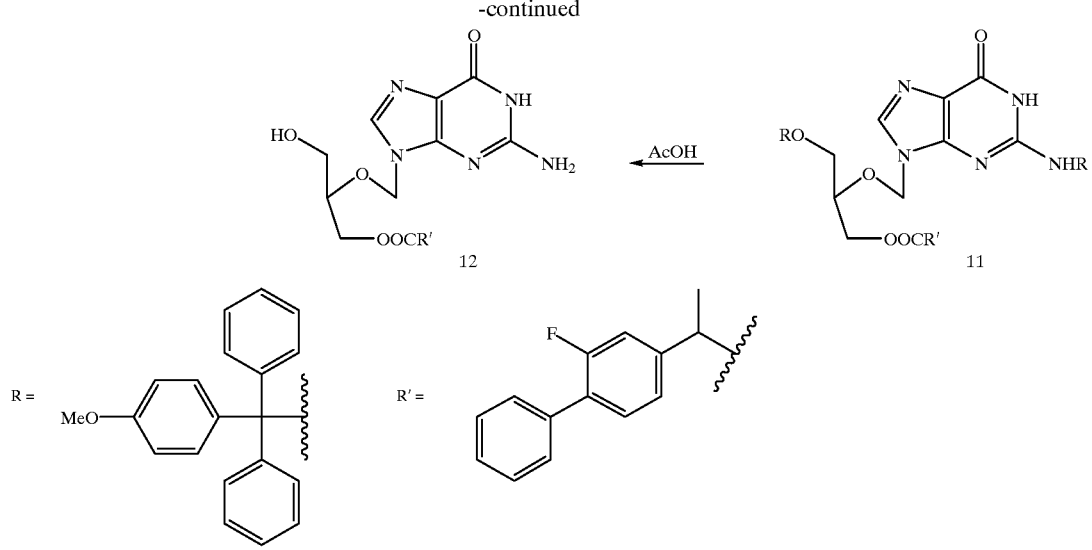
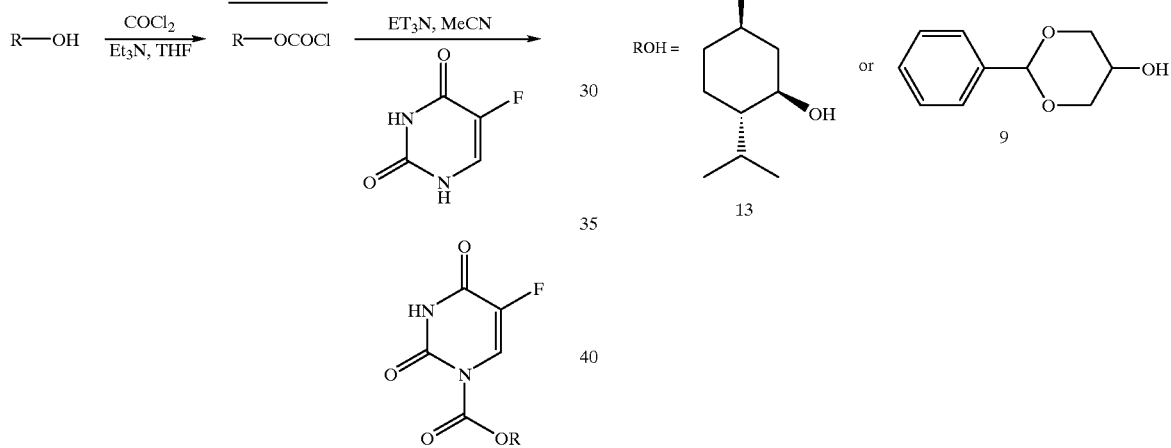
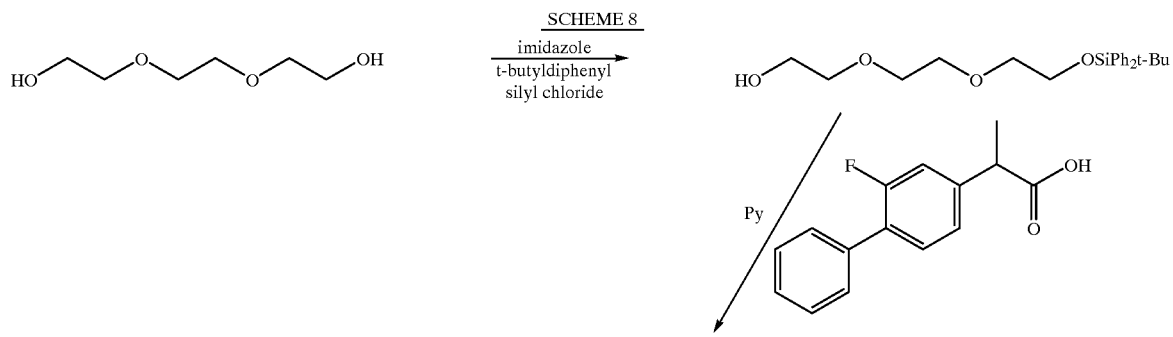

-continued
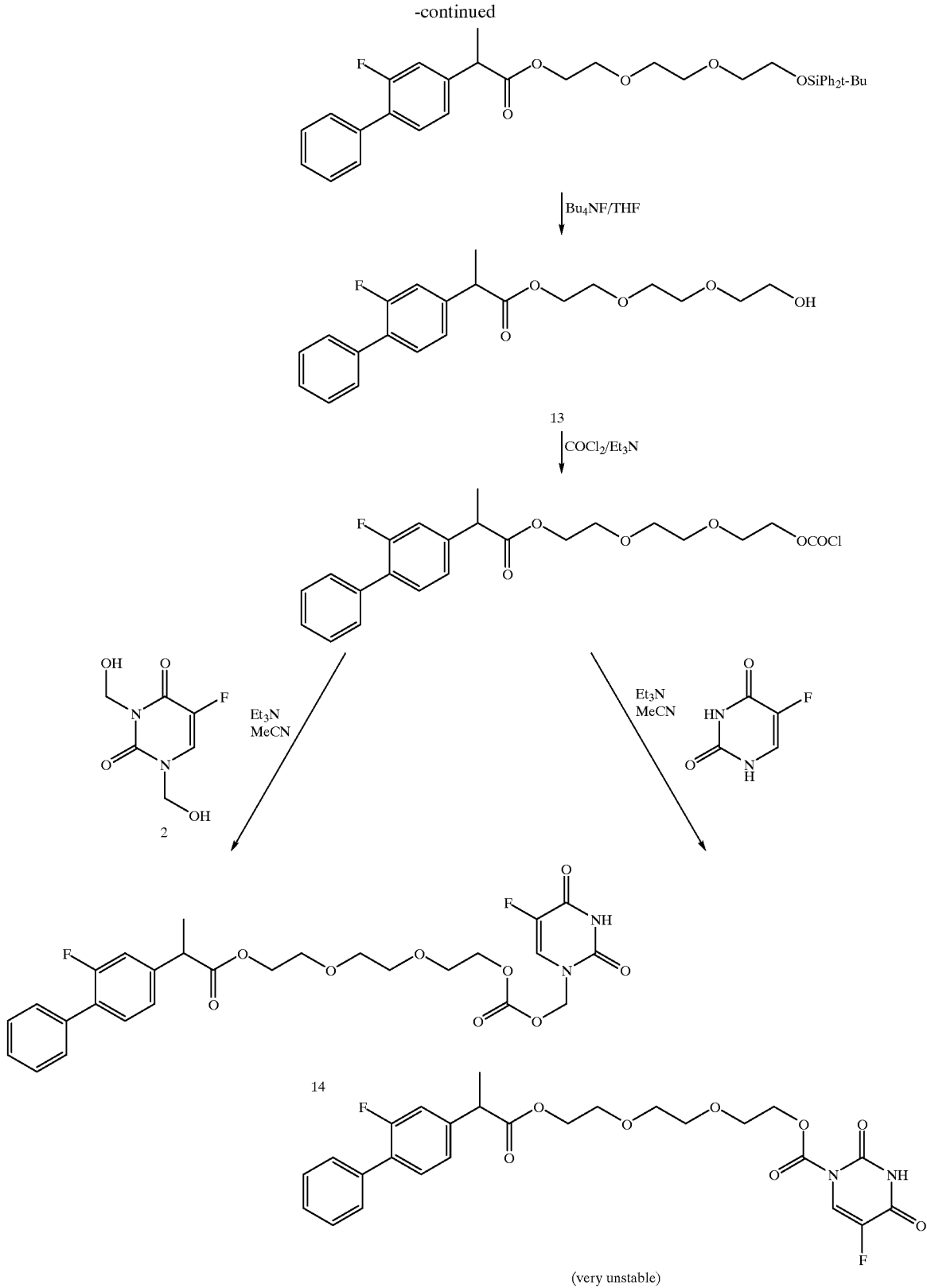

33
34
SCHEME 9
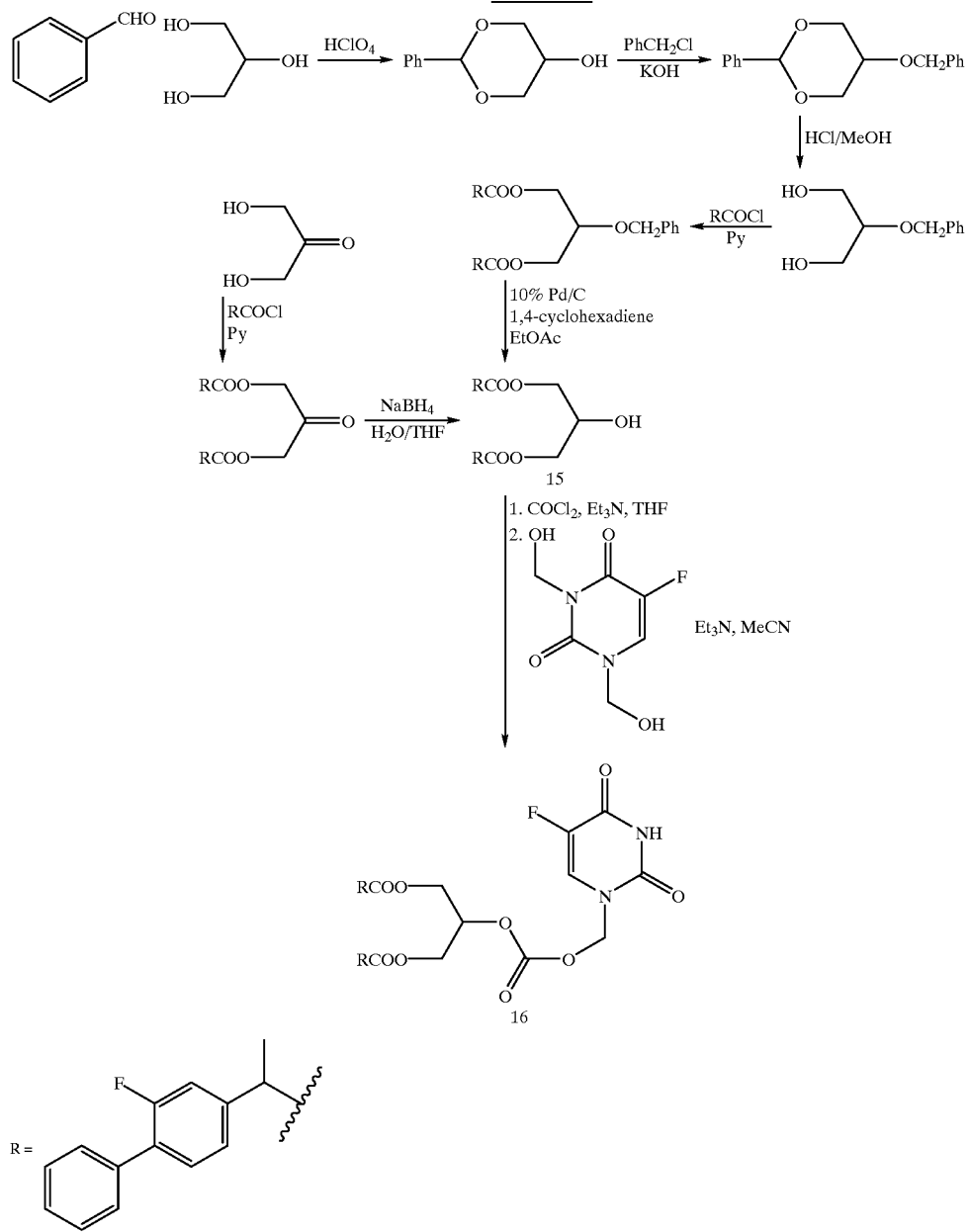

SCHEME 10
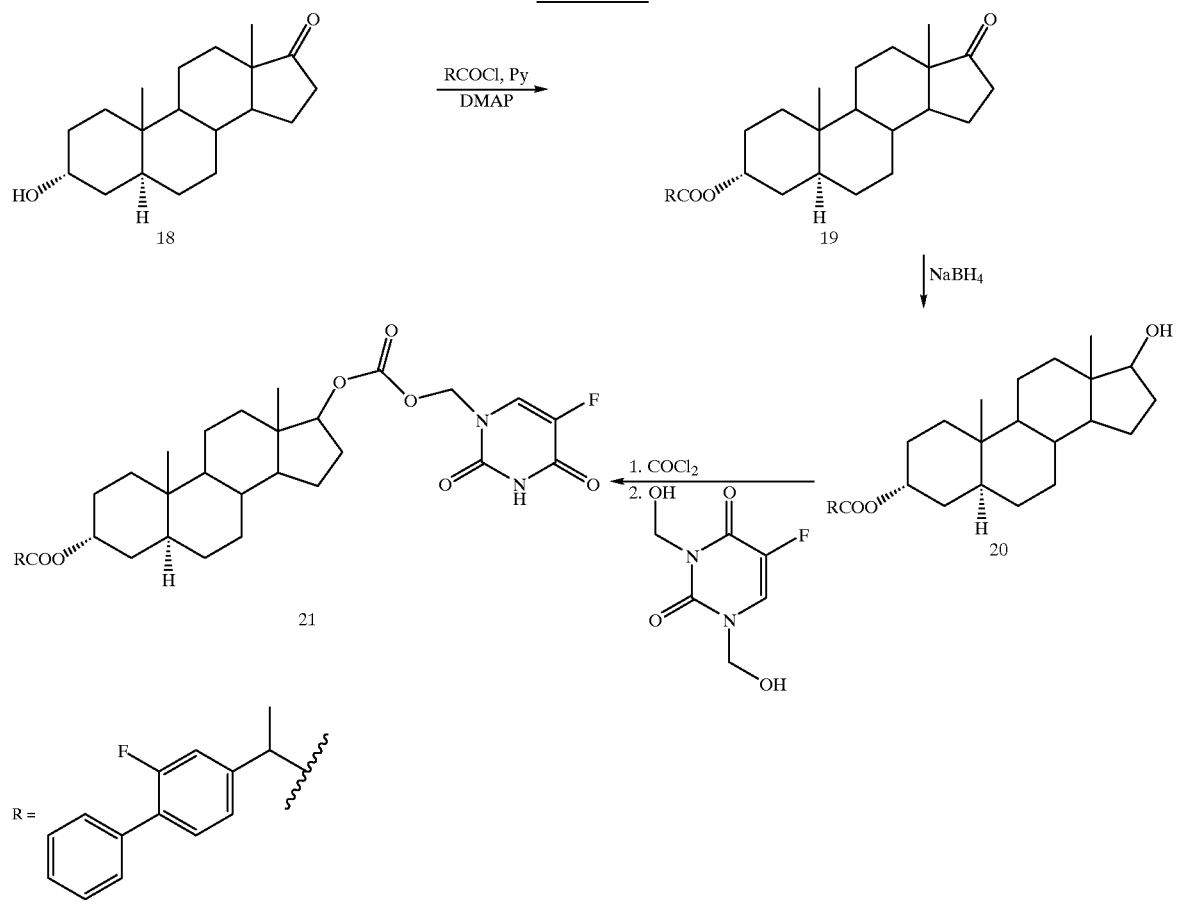
SCHEME 11
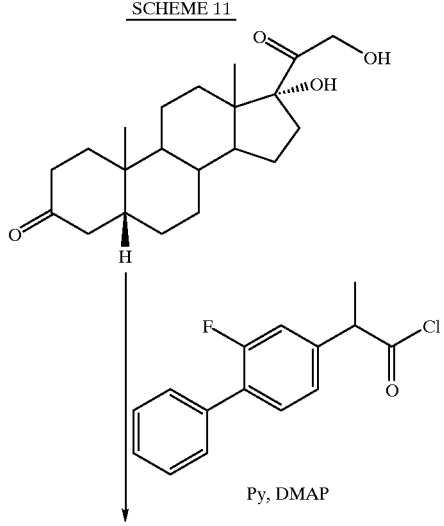

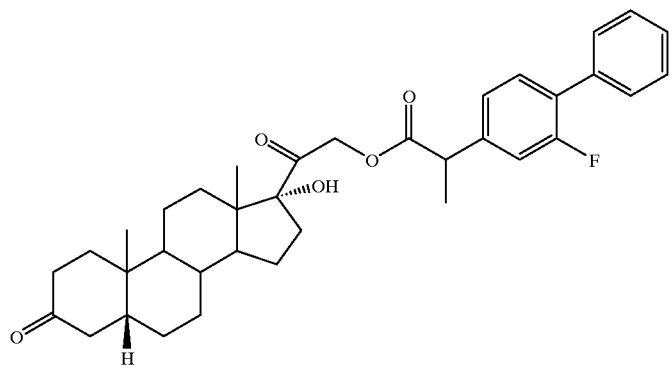
SCHEME 12
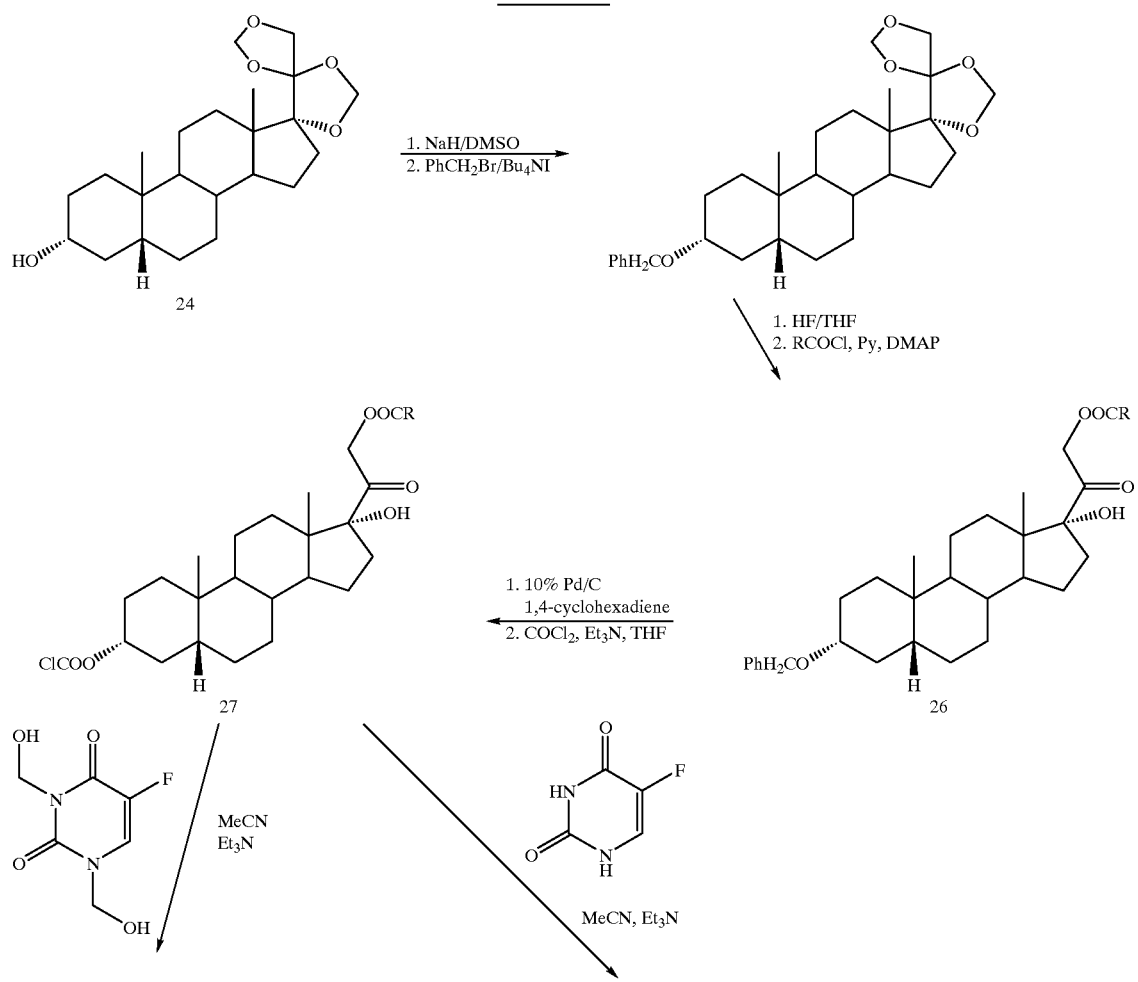

-continued
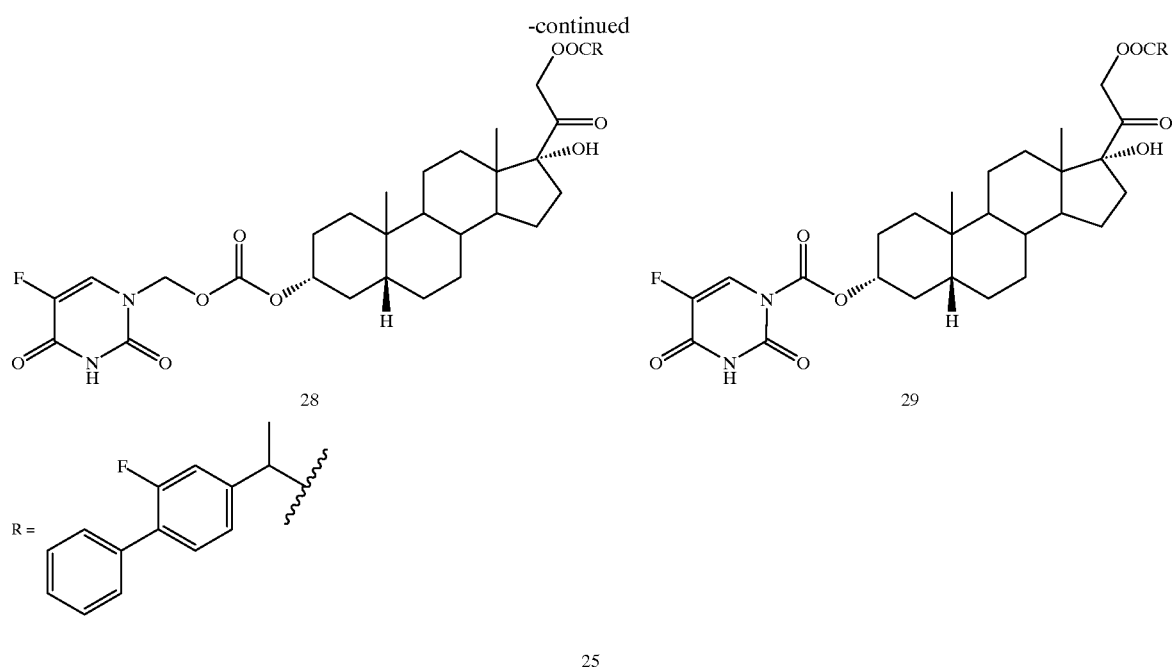
SCHEME 13
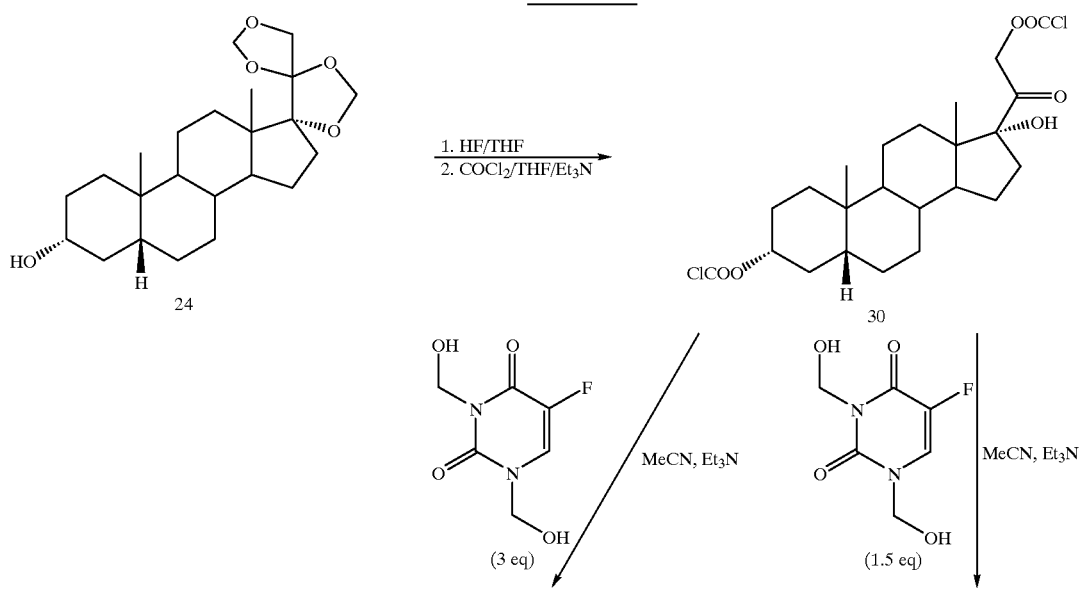

-continued
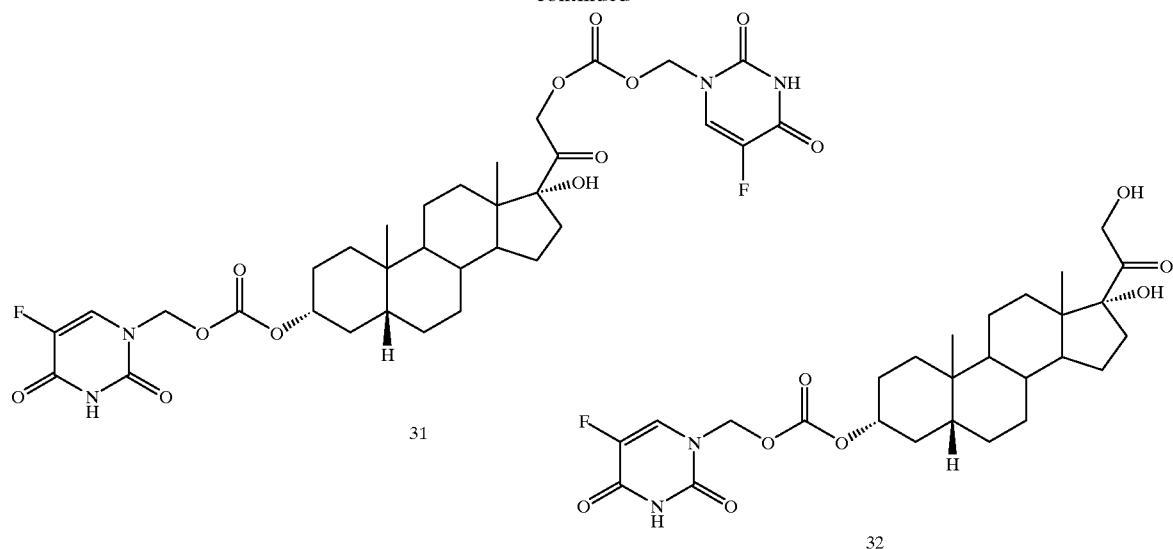
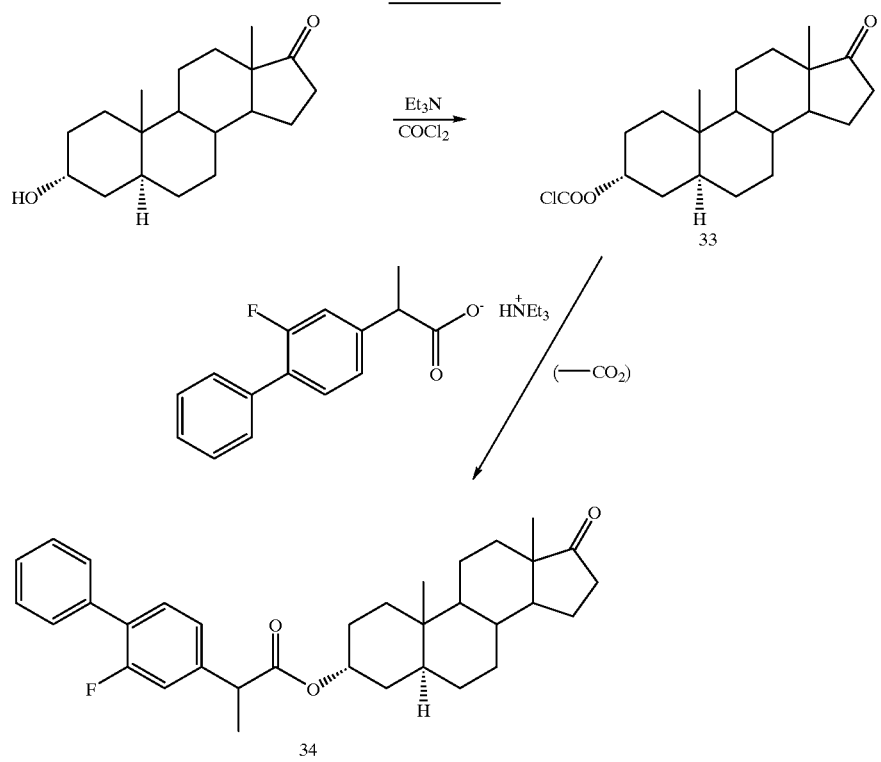

SCHEME 15
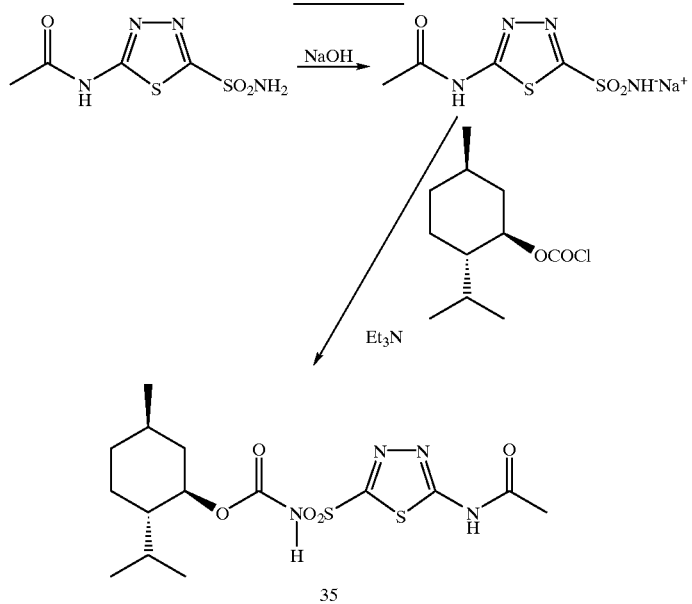
SCHEME 16
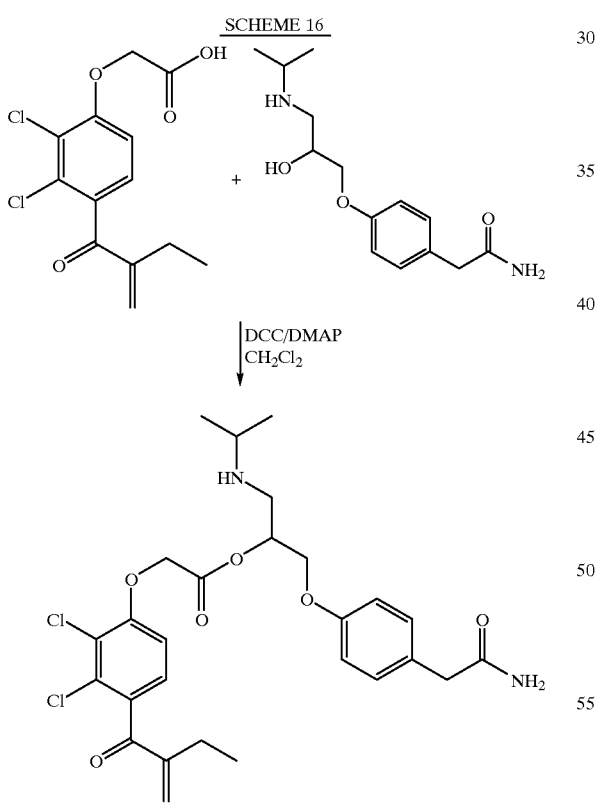

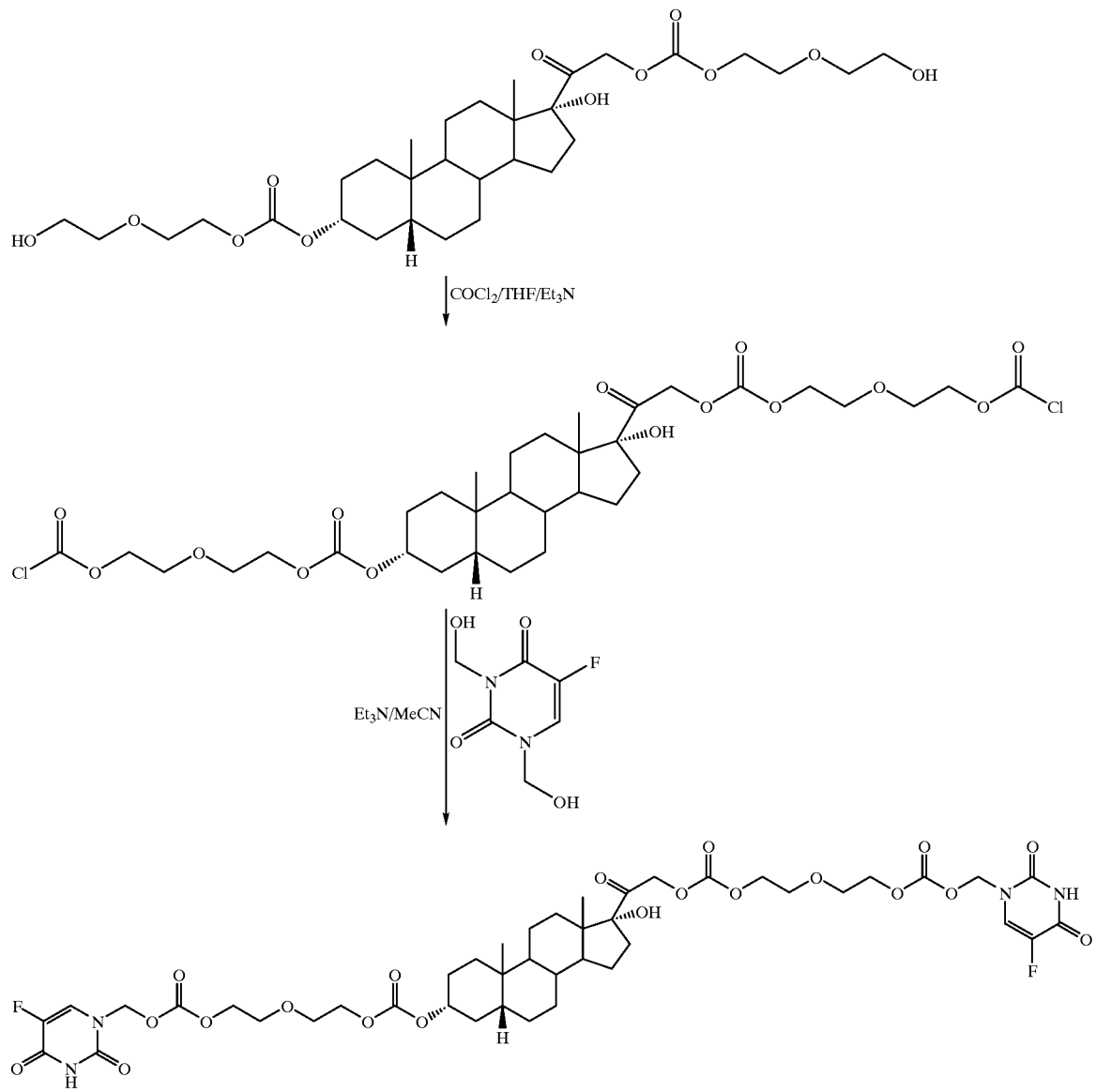
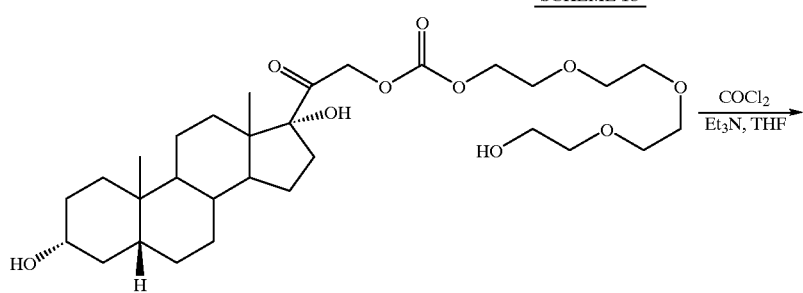

-continued
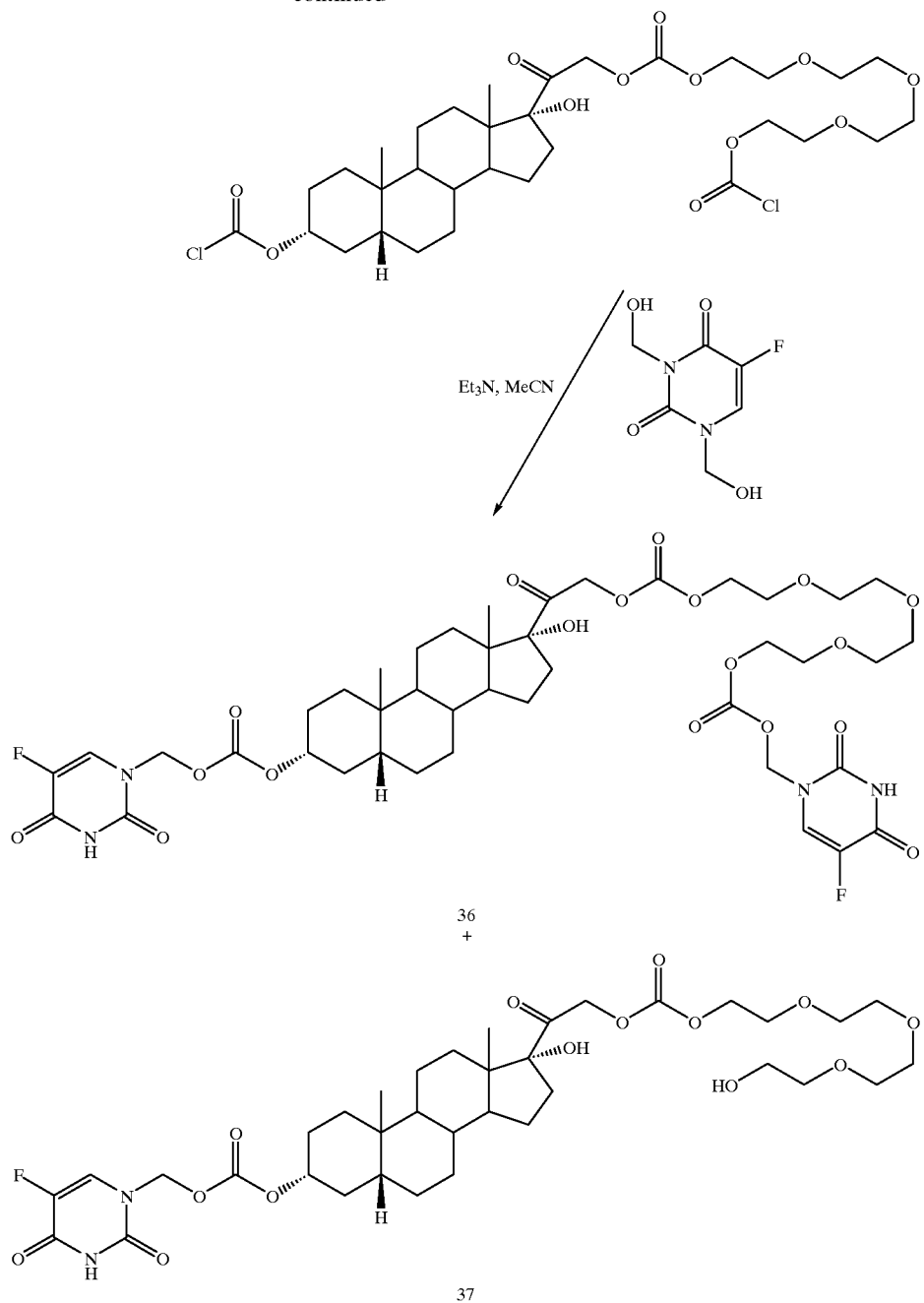

SCHEME 19

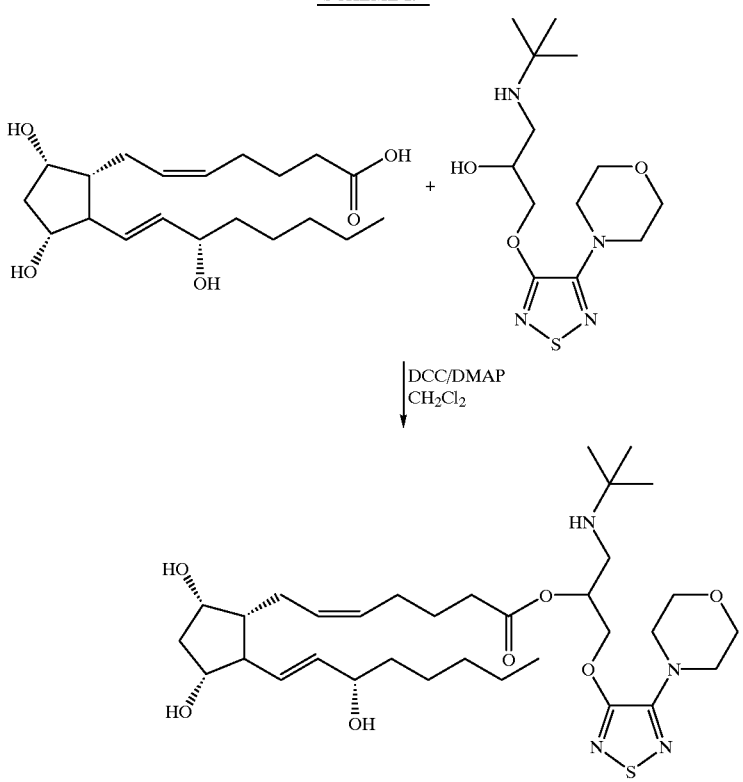

The purpose of the above description and examples are to illustrate some embodiments of the present invention without implying any limitation. It will be apparent to those of skill in the art that various modifications and variations may be made to the composition and method of the present invention without departing from the spirit or scope of the invention. All patents and publications cited herein are incorporated by reference in their entireties.

We claim:

1. A sustained release, and substantially inactive codrug, comprising at least two drugs ionically or covalently linked to one another wherein each active drug is regenerated upon bond cleavage.

2. A codrug according to claim 1, wherein said codrug comprises suramin ionically linked to amiloride.

3. A codrug according to claim 1, wherein said codrug is in injectable form.

4. A codrug according to claim 3, wherein said injectable form is selected from the group consisting of liposomes, suspensions, microsphere and nanoparticles.

5. A codrug according to claim 1, wherein said codrug is in solid form.

6. A codrug according to claim 1, wherein said codrug is applied topically.

7. A codrug according to claim 1, wherein said codrug applied topically is in a form selected from the group consisting of a transdermal patch, ointment, cream, suspension, liquid, elixir and eye drop.

8. A codrug according to claim 1, wherein said codrug is administered by a method selected from the group consisting of injection, inhalation, implantation, applied as a nasal spray, applied rectally, applied vaginally, ingested orally and applied topically.

9. A codrug according to claim 1, wherein said codrug is fixed to an implantable device.

10. A codrug according to claim 1, wherein said codrug is a coating on an implantable device.

11. A codrug according to claim 10, wherein said implantable device is or is attached to a suture.

12. A codrug according to claim 1, wherein said codrug is in the form of a nonerodible delivery vehicle.

13. A codrug according to claim 12, wherein said nonerodible delivery vehicle comprises polyvinyl alcohol.

14. A codrug according to claim 12, wherein said codrug comprises from 0.1 to up to about 100% of said nonerodible delivery vehicle.

15. A codrug according to claim 1, wherein said codrug is in the form of an erodible delivery vehicle.

16. A codrug according to claim 1, wherein said codrug comprises one molecule of suramin ionically linked to six molecules of amiloride.

17. A codrug according to claim 15, wherein said codrug comprises from 0.1 to up to about 100% of said erodible delivery vehicle.

18. A codrug according to claim 1, wherein said codrug comprises ethacrynic acid covalently linked to atenolol.

19. A codrug according to claim 1, wherein said codrug comprises 17α-21-trihydroxy-5β pregnane-20-one (THS) covalently linked to form a codrug with 5FU and diethylene glycol.

20. A codrug according to claim 1, wherein said codrug comprises 17α-21-trihydroxy-5β pregnane-20-one (THS) covalently linked to form a codrug with 5FU and tetraethylene glycol.

21. A codrug according to claim 1, wherein said codrug comprises prostaglandin F2 alpha (PGF2α) covalently linked to form a codrug with timolol (TM).

22. A method of inhibiting angiogenesis comprising administering an effective amount of a codrug according to claim 2 to a patient in need of angiogenesis inhibition.

23. A codrug according to claim 1, which is essentially insoluble in body fluids.

24. A codrug according to claim 1, wherein each drug is released in equimolar amounts.

25. A codrug according to claim 1, wherein at least three drugs are ionically or covalently linked to one another via an ionic bond or covalent bond.

26. A codrug according to claim 1, wherein release of the active drugs follows pseudo zero order kinetics.

27. A codrug according to claim 1, wherein the drugs are ionically linked and release of the active drugs follows pseudo zero order kinetics for about 10 days to about 6 weeks.

28. A codrug according to claim 27, wherein release of each active drug follows pseudo zero order kinetics for about 3 weeks.

29. A codrug according to claim 1, which is soluble in body fluids.

30. A composition comprising a codrug according to claim 1, and a pharmaceutically acceptable carrier.

31. A sustained release, and substantially inactive codrug, comprising at least two drugs covalently linked to one another wherein each active drug is regenerated upon bond cleavage.

32. A codrug according to claim 31, wherein said codrug is a coating on an implantable device.

33. A codrug according to claim 32, wherein said implantable device is a suture.

34. A codrug according to claim 31, wherein said codrug is in the form of a nonerodible delivery vehicle.

35. A codrug according to claim 34, wherein the nonerodible delivery vehicle comprises polyvinyl alcohol.

36. A codrug according to claim 31, wherein each drug is released in equimolar amounts.

37. A codrug according to claim 31, wherein release of each active drug follows pseudo zero order kinetics for about three weeks.

* * * * *